US008124781B2

(12) United States Patent
Siesel

(10) Patent No.: US 8,124,781 B2
(45) Date of Patent: Feb. 28, 2012

(54) PROCESSES FOR PRODUCING CYCLOALKYLCARBOXAMIDO-PYRIDINE BENZOIC ACIDS

(75) Inventor: David Siesel, San Diego, CA (US)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 461 days.

(21) Appl. No.: 12/327,915

(22) Filed: Dec. 4, 2008

(65) Prior Publication Data
US 2009/0176989 A1 Jul. 9, 2009

Related U.S. Application Data

(60) Provisional application No. 61/012,181, filed on Dec. 7, 2007, provisional application No. 61/109,573, filed on Oct. 30, 2008.

(51) Int. Cl.
C07D 405/12 (2006.01)
(52) U.S. Cl. .................................. 546/283.7
(58) Field of Classification Search ................ 546/283.7
See application file for complete search history.

(56) References Cited

U.S. PATENT DOCUMENTS

| 6,426,331 | B1 | 7/2002 | McKinney et al. |
| 6,479,483 | B2 | 11/2002 | Bos et al. |
| 6,770,637 | B2 | 8/2004 | Godel et al. |
| 7,407,976 | B2 | 8/2008 | Miller et al. |
| 7,495,103 | B2 | 2/2009 | Hadida-Ruah et al. |
| 7,553,855 | B2 | 6/2009 | Young et al. |
| 7,598,412 | B2 | 10/2009 | Hadida Ruah et al. |
| 7,645,789 | B2 | 1/2010 | Hadida Ruah et al. |
| 7,659,268 | B2 | 2/2010 | Hadida-Ruah et al. |
| 7,671,221 | B2 | 3/2010 | Hadida Ruah et al. |
| 7,691,902 | B2 | 4/2010 | Hadida Ruah et al. |
| 7,741,321 | B2 | 6/2010 | Hadida Ruah et al. |
| 7,754,739 | B2 | 7/2010 | Hadida Ruah et al. |
| 7,776,905 | B2 | 8/2010 | Hadidia Ruah |
| 7,846,951 | B2 | 12/2010 | Miller et al. |
| 7,956,052 | B2 | 6/2011 | Hadidia Ruah |
| 7,973,038 | B2 | 7/2011 | Hadidia Ruah |
| 7,973,169 | B2 | 7/2011 | Hadidia Ruah |
| 7,977,322 | B2 | 7/2011 | Hadidia Ruah |
| 7,999,113 | B2 | 8/2011 | Hadidia-Ruah et al. |
| 2003/0125315 | A1 | 7/2003 | Mjalli et al. |
| 2005/0059687 | A1 | 3/2005 | Makings et al. |
| 2005/0070718 | A1 | 3/2005 | Lubisch et al. |
| 2005/0113423 | A1 | 5/2005 | VanGoor |
| 2005/0176789 | A1 | 8/2005 | Hadida Ruah et al. |
| 2006/0052358 | A1 | 3/2006 | Hadida Ruah et al. |
| 2007/0105833 | A1 | 5/2007 | Hadida Ruah et al. |
| 2007/0238775 | A1 | 10/2007 | Hadidia Ruah et al. |
| 2007/0244159 | A1 | 10/2007 | Hadida Ruah et al. |
| 2007/0264196 | A1 | 11/2007 | Hadida Ruah et al. |
| 2008/0071095 | A1 | 3/2008 | Hadida-Ruah et al. |
| 2008/0161371 | A1 | 7/2008 | Hadida-Ruah et al. |
| 2008/0176899 | A1 | 7/2008 | Hadida Ruah et al. |
| 2008/0286204 | A1 | 11/2008 | Hadida-Ruah et al. |
| 2008/0306062 | A1 | 12/2008 | Hadida Ruah et al. |
| 2009/0099230 | A1 | 4/2009 | DeMattei et al. |
| 2009/0105272 | A1 | 4/2009 | Grootenhuis et al. |
| 2009/0143381 | A1 | 6/2009 | Hadida Ruah et al. |
| 2009/0170905 | A1 | 7/2009 | Keshavarz et al. |
| 2009/0176839 | A1 | 7/2009 | Keshavarz et al. |
| 2009/0221597 | A1 | 9/2009 | Hadida Ruah et al. |
| 2009/0227797 | A1 | 9/2009 | Hadida Ruah et al. |
| 2009/0246137 | A1 | 10/2009 | Hadida Ruah et al. |
| 2009/0246820 | A1 | 10/2009 | Singh et al. |
| 2009/0253736 | A1 | 10/2009 | Hadida Ruah et al. |
| 2009/0298876 | A1 | 12/2009 | Hadida Ruah et al. |
| 2010/0036130 | A1 | 2/2010 | Siesel et al. |
| 2010/0069434 | A1 | 3/2010 | Young et al. |
| 2010/0074949 | A1 | 3/2010 | Rowe et al. |
| 2010/0087435 | A1 | 4/2010 | Hadida Ruah et al. |
| 2010/0087490 | A1 | 4/2010 | Young et al. |
| 2010/0105739 | A1 | 4/2010 | Hadida Ruah et al. |
| 2010/0113508 | A1 | 5/2010 | Binch et al. |
| 2010/0113509 | A1 | 5/2010 | Binch et al. |
| 2010/0113555 | A1 | 5/2010 | Hadida Ruah et al. |
| 2010/0125090 | A1 | 5/2010 | Hadida Ruah et al. |
| 2010/0130547 | A1 | 5/2010 | Zhang et al. |
| 2010/0144798 | A1 | 6/2010 | VanGoor |
| 2010/0168094 | A1 | 7/2010 | Binch et al. |
| 2010/0168158 | A1 | 7/2010 | Binch et al. |
| 2010/0184739 | A1 | 7/2010 | Sheth et al. |
| 2010/0210638 | A1 | 8/2010 | Hadida Ruah et al. |
| 2010/0227888 | A1 | 9/2010 | Hadida Ruah et al. |
| 2010/0249113 | A1 | 9/2010 | Hadida Ruah et al. |
| 2010/0249180 | A1 | 9/2010 | Gallardo-Godoy et al. |
| 2010/0256184 | A1 | 10/2010 | Rowe et al. |
| 2010/0261750 | A1 | 10/2010 | Binch et al. |
| 2010/0267768 | A1 | 10/2010 | Demattei et al. |
| 2010/0331344 | A1 | 12/2010 | Hadidia Ruah et al. |
| 2011/0008259 | A1 | 1/2011 | Binch et al. |
| 2011/0060024 | A1 | 3/2011 | Hadidia Ruah et al. |
| 2011/0064811 | A1 | 3/2011 | Hurter et al. |
| 2011/0065928 | A1 | 3/2011 | Ambhaikar et al. |
| 2011/0071206 | A1 | 3/2011 | Hadidia Ruah et al. |
| 2011/0098311 | A1 | 4/2011 | VanGoor et al. |
| 2011/0123449 | A1 | 5/2011 | Zhang et al. |
| 2011/0124869 | A1 | 5/2011 | Ambhaikar et al. |
| 2011/0144123 | A1 | 6/2011 | Miller et al. |
| 2011/0172229 | A1 | 7/2011 | Hadidia-Ruah et al. |
| 2011/0177999 | A1 | 7/2011 | Singh et al. |

FOREIGN PATENT DOCUMENTS

EP 591830 A1 4/1994

(Continued)

OTHER PUBLICATIONS

International Search Report for corresponding PCT Application No. PCT/US2008/085458 filed on Dec. 4, 2008. Jingjun, Yin, et al. "A General and efficient 2-amination of pyridines and quinolines", Journal of Organic Chemistry, 72(12), 4554-4557, (2007).

Primary Examiner — Patricia Morris
(74) Attorney, Agent, or Firm — Michael J. DiVerdi

(57) ABSTRACT

The present invention relates to a process of providing the 3-(6-(1-(2,2-difluorobenzo[d][1,3]dioxol-5-yl)cyclopropanecarboxamido)-3-methylpyridin-2-yl)benzoic acid in substantially free form (Compound 1).

35 Claims, 11 Drawing Sheets

FOREIGN PATENT DOCUMENTS

| | | |
|---|---|---|
| EP | 0081756 | 10/2010 |
| JP | 2003155285 A2 | 5/2003 |
| WO | 9506046 A2 | 3/1995 |
| WO | 9619444 A1 | 6/1996 |
| WO | 9736876 A1 | 10/1997 |
| WO | 9807420 A1 | 2/1998 |
| WO | 9828980 A1 | 7/1998 |
| WO | 9847868 A1 | 10/1998 |
| WO | 9941405 A1 | 8/1999 |
| WO | 9964394 A1 | 12/1999 |
| WO | 0016798 A1 | 3/2000 |
| WO | 0050398 A1 | 8/2000 |
| WO | 0050401 A1 | 8/2000 |
| WO | 0154690 A1 | 8/2001 |
| WO | 0156989 A2 | 8/2001 |
| WO | 0254690 A1 | 8/2001 |
| WO | 0181317 A1 | 11/2001 |
| WO | 0183517 A1 | 11/2001 |
| WO | 0192235 A1 | 12/2001 |
| WO | 0216324 A1 | 2/2002 |
| WO | 0230875 A1 | 4/2002 |
| WO | 0234739 A1 | 5/2002 |
| WO | 0238107 A2 | 5/2002 |
| WO | 02079134 A1 | 10/2002 |
| WO | 02085458 A2 | 10/2002 |
| WO | 03006016 A2 | 1/2003 |
| WO | 03007888 A2 | 1/2003 |
| WO | 03007945 A1 | 1/2003 |
| WO | 03042191 A1 | 5/2003 |
| WO | 03055482 A1 | 7/2003 |
| WO | 03084997 A2 | 10/2003 |
| WO | 03105788 A2 | 12/2003 |
| WO | 2005000300 A1 | 1/2004 |
| WO | 2004035571 A1 | 4/2004 |
| WO | 2004041163 A2 | 5/2004 |
| WO | 2004063179 A1 | 7/2004 |
| WO | 2004099168 A2 | 11/2004 |
| WO | 2005030755 A1 | 4/2005 |
| WO | 2005044797 A1 | 5/2005 |
| WO | 2005075435 A2 | 8/2005 |
| WO | 2006014012 A2 | 2/2006 |
| WO | 2006040520 A1 | 4/2006 |
| WO | 2006080884 A1 | 8/2006 |
| WO | 2006129199 A1 | 12/2006 |
| WO | 2007028654 A2 | 3/2007 |
| WO | 2007039420 A1 | 4/2007 |
| WO | 2007056341 A1 | 5/2007 |

PROCESSES FOR PRODUCING CYCLOALKYLCARBOXAMIDO-PYRIDINE BENZOIC ACIDS

CROSS REFERENCE TO RELATED APPLICATIONS

This application claims the benefit under 35 U.S.C. §119 to U.S. provisional patent application Ser. Nos. 61/012,181, filed Dec. 7, 2007, and 61/109,573, filed Oct. 30, 2008, the entire contents of both applications are incorporated herein by reference.

TECHNICAL FIELD OF THE INVENTION

The present invention relates to processes for the preparation of compounds useful for treating a CFTR mediated disease such as cystic fibrosis.

BACKGROUND OF THE INVENTION

CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl- channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. Infact, this cellular phenomenon of defective ER processing of ABC transporters by the ER machinery, has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, JP et al., TIPS, 21, pp. 466-469 (2000); Bross P., et al., Human Mut., 14, pp. 186-198 (1999)].

3-(6-(1-(2,2-Difluorobenzo[d][1,3]dioxol-5-yl)cyclopropanecarboxamido)-3-methylpyridin-2-yl)benzoic acid in salt form is disclosed in International PCT Publication WO 2007056341 (said publication being incorporated herein by reference in its entirety) as a modulator of CFTR activity and thus useful in treating CFTR-mediated diseases such as cystic fibrosis. There remains, however, a need for economical processes for the preparation of the cycloalkylcarboxamidopyridine benzoic acids described herein.

SUMMARY OF THE INVENTION

As described herein, the present invention provides processes for preparing CFTR correctors useful in the treatment of cystic fibrosis. Such compounds include 3-(6-(1-(2,2-difluorobenzo[d][1,3]dioxol-5-yl)cyclopropanecarboxamido)-3-methylpyridin-2-yl)benzoic acid (hereinafter "Compound 1") which has the structure below:

Compound 1

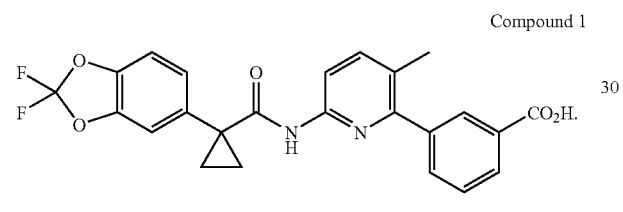

Compound 1 and pharmaceutically acceptable compositions thereof are useful for treating or lessening the severity of a variety of CFTR mediated diseases. Compound 1 is in a substantially crystalline and salt free form referred to as Form I as described and characterized herein.

DETAILED DESCRIPTION OF THE INVENTION

Figure 1:
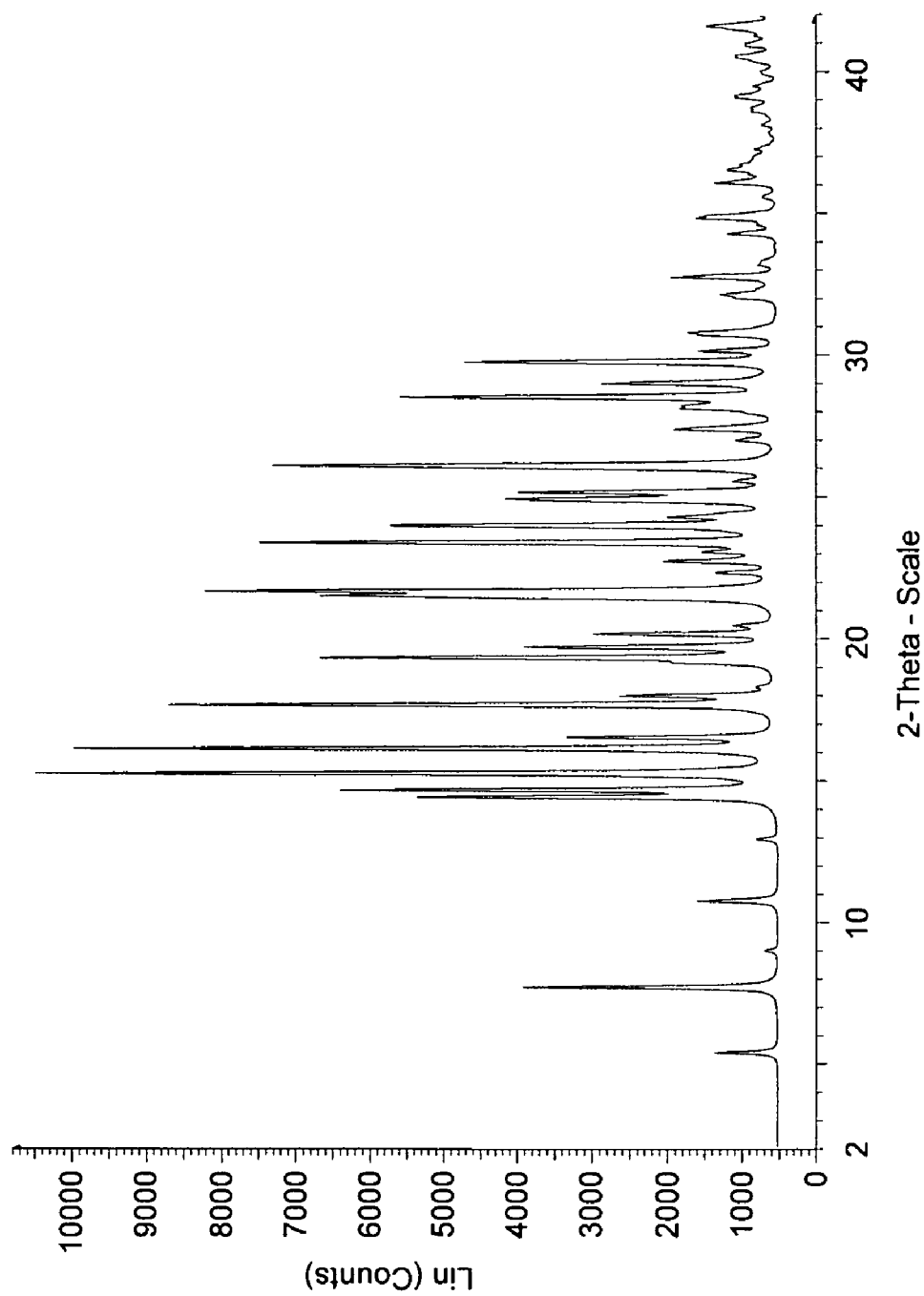
FIG. 1 is an X-ray diffraction pattern calculated from a single crystal structure of Compound 1 in Form I.

The present invention relates to a process for preparing Compound 1:

Compound 1

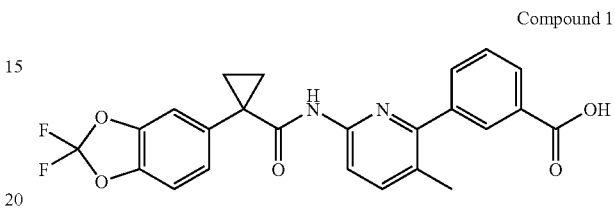

comprising the steps of:
i) providing 2-bromo-3-methylpyridine (compound 2) and 3-(t-butoxycarbonyl)phenylboronic acid (compound 3),

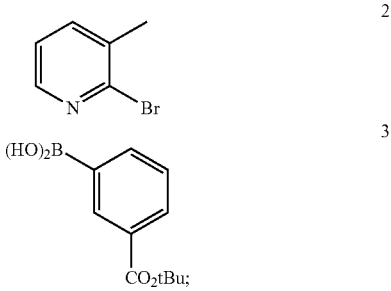

ii) cross coupling compound 2 and compound 3 in a biphasic mixture comprising water, an organic solvent, a base, and a transition metal catalyst to produce compound 4,

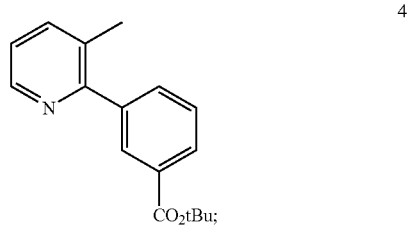

iii) oxidizing compound 4 to produce compound 5,

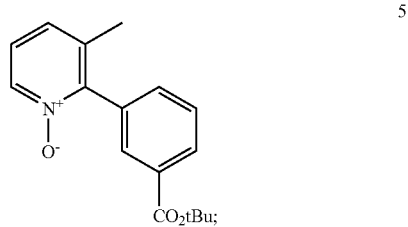

iv) adding an amine group to the 6 position of the pyridyl moiety to produce compound 6,

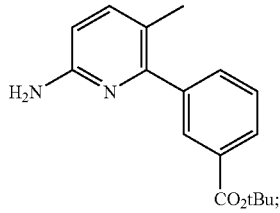
6 v) reacting compound 6 with compound 7,

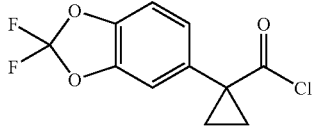
7 in an organic solvent in the presence of a base to produce compound 8,

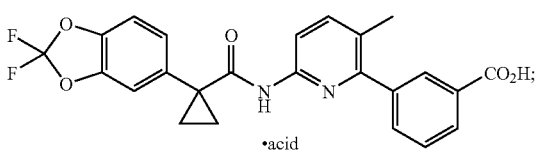
8 vi) de-esterifying compound 8 in a biphasic mixture comprising water, an organic solvent, and an acid to produce compound 9,

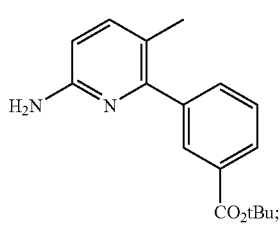
9 vii) slurrying or dissolving compound 9 in an appropriate solvent for an effective amount of time to produce Compound 1, which is a free form of compound 9 and is sometimes referred to as Form I as characterized herein.

In other embodiments, the process for preparing Compound 1 comprises the step of:

i) reacting compound 6,

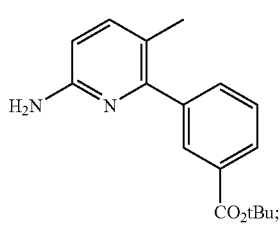
6 with compound 7,

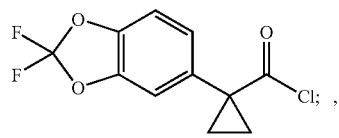
7 in an organic solvent in the presence of a base to produce compound 8,

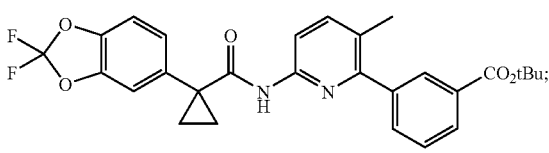
8 ii) de-esterifying compound 8 in a biphasic mixture comprising water, an organic solvent, and an acid to produce compound 9,

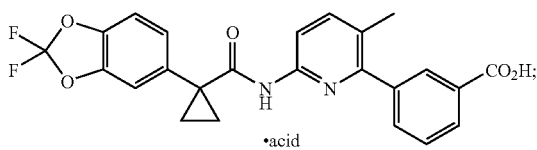
9 iii) slurrying or dissolving compound 9 in an appropriate solvent for an effective amount of time to produce Compound 1.

The present invention also provides a process for preparing a compound of formula 1:

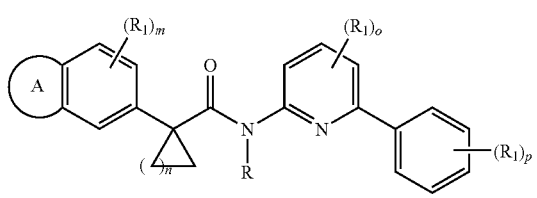
1 comprising the step of:

ia) reacting a compound of formula 6a:

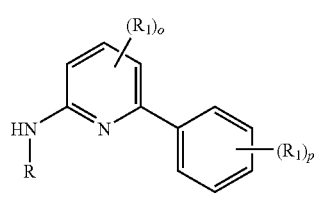

wherein,

R is H, $C_{1-6}$ aliphatic, aryl, aralkyl, heteroaryl, cycloalkyl, or heterocycloalkyl;

$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;

$R^J$ is hydrogen or $C_{1-6}$ aliphatic;

o is an integer from 0 to 3 inclusive; and p is an integer from 0 to 5 inclusive;

with a compound of formula 7a:

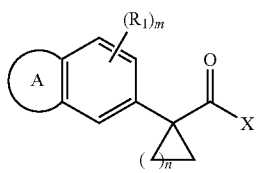

7a wherein,

A is a fused cycloalkyl, heterocycloalkyl, aryl, or heteroaryl ring;

$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;

$R^J$ is hydrogen or $C_{1-6}$ aliphatic;

m is an integer from 0 to 3 inclusive;

n is an integer from 1 to 4 inclusive; and

X is a halo or OH;

in an organic solvent in the presence of a base.

The present invention provides a process for preparing a compound of formula 6a:

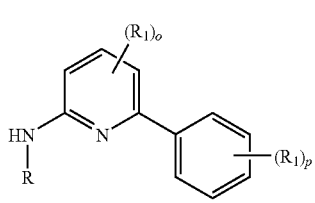

6a wherein,

R is H, $C_{1-6}$ aliphatic, aryl, aralkyl, heteroaryl, cycloalkyl, or heterocycloalkyl;

$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;

$R^J$ is hydrogen or $C_{1-6}$ aliphatic;

o is an integer from 0 to 3 inclusive; and p is an integer from 0 to 5 inclusive;

comprising the steps of:

ib) providing compound 2a and compound 3a,

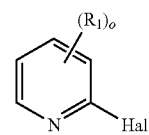

2a

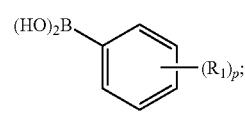

3a wherein, $R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;

$R^J$ is hydrogen or $C_{1-6}$ aliphatic;

o is an integer from 0 to 4 inclusive; and p is an integer from 0 to 5 inclusive;

iib) cross coupling compound 2a and compound 3a in a biphasic mixture comprising water, an organic solvent, a base, and a transition metal catalyst to produce compound 4a,

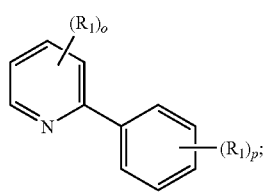

4a wherein, $R_1$, o, and p are as defined for compounds 2a and 3a above;

iiib) oxidizing compound 4a to produce compound 5a,

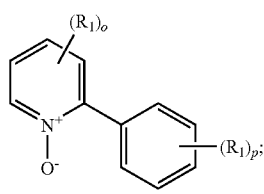

5a wherein, $R_1$, o, and p are as defined for compounds 2a and 3a above;

ivb) adding an amine group to the 6 position of the pyridyl moiety to produce compound 6a,

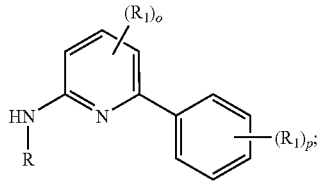

6a wherein,

R is H, $C_{1-6}$ aliphatic, aryl, aralkyl, heteroaryl, cycloalkyl, or heterocycloalkyl; and $R_1$, o, and p are as defined for compounds 2a and 3a above.

The present invention also provides a process for preparing a compound of formula 7a:

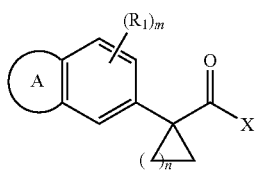

7a wherein,

A is a fused cycloalkyl, heterocycloalkyl, aryl, or heteroaryl ring;

$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;

$R^J$ is hydrogen or $C_{1-6}$ aliphatic;

m is an integer from 0 to 3 inclusive;

n is an integer from 1 to 4 inclusive; and

X is a halide or OH;

comprising the steps of ib) reducing Compound 10b:

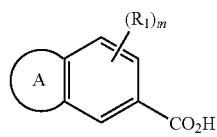

10b wherein,

A is a fused cycloalkyl, heterocycloalkyl, aryl, or heteroaryl ring;

$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;

$R^J$ is hydrogen or $C_{1-6}$ aliphatic; and m is an integer from 0 to 3 inclusive, with a reducing agent to produce Compound 11b:

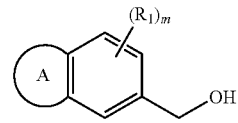

11b wherein, ring A, $R_1$, and m are as defined in Compound 10b above;

iib) reacting Compound 11b with a halogenating agent to produce Compound 12b:

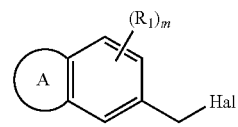

12b wherein, ring A, $R_1$, and m are as defined in Compound 10b above, and Hal is a halide;

iiib) reacting Compound 12b with a cyanide to produce Compound 13b:

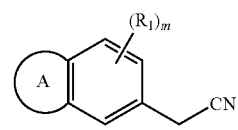

13b wherein, ring A, $R_1$, and m are as defined in Compound 10b above;

ivb) reacting Compound 13b with a compound of formula 13bb in the presence of a base:

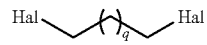

13bb wherein,

Hal is a halide; and q is an integer from 0 to 3 inclusive; to produce a compound of formula 14b:

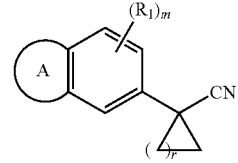

14b wherein, r is an integer from 1 to 4 inclusive; and ring A, $R_1$, and m are as defined in Compound 10b above;

vb) sequentially reacting Compound 14b with a hydroxide base and acid to form Compound 15b, which is compound 7a when X=OH:

15b wherein, r, ring A, $R_1$, and m are as defined in Compound 14b above; and vib) reacting Compound 15b with a halogenating agent to form Compound 16b, which is compound 7a when X=halide:

16b wherein,

Hal is halide; and r, ring A, $R_1$, and m are as defined in Compound 14b above.

The present invention also provides a process for preparing Compound 1 from compound 9 below:

1

9
·HCl said process comprising the step of slurrying compound 9 in an appropriate solvent and stirring for an effective amount of time to produce Compound 1.

The present invention also provides a process for preparing Compound 1 from compound 9 below:

1

9
·HCl said process comprising the steps of slurrying compound 9, adding aqueous NaOH, and effecting recrystallization to produce Compound 1.

The present invention also provides a compound of formula 6b:

6b wherein,

R is H, $C_{1-6}$ aliphatic, aryl, aralkyl, heteroaryl, cycloalkyl, or heterocycloalkyl;

$R_1$ and $R_2$ are independently selected from —$R^J$, —$OR^J$, —$N(R^J)_2$, —$NO_2$, halogen, —CN, —$C_{1-4}$haloalkyl, —$C_{1-4}$ haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;

$R^J$ is hydrogen or $C_{1-6}$ aliphatic;

o is an integer from 0 to 3 inclusive; and p is an integer from 0 to 5 inclusive.

Definitions

As used herein, the following definitions shall apply unless otherwise indicated.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

As used herein "crystalline" refers to compounds or compositions where the structural units are arranged in fixed geometric patterns or lattices, so that crystalline solids have rigid long range order. The structural units that constitute the crystal structure can be atoms, molecules, or ions. Crystalline solids show definite melting points.

As art-recognized the bidentate ligand (dppf) as in Pd(dppf)Cl$_2$ stands for diphenylphosphinoferrocene and as the formula $Ph_2PC_5H_4FeC_5H_4PPh_2$.

The term "modulating" as used herein means increasing or decreasing, e.g. activity, by a measurable amount.

As described herein, a bond drawn from a substituent to the center of one ring within a multiple-ring system (as shown below) represents substitution of the substituent at any substitutable position in any of the rings within the multiple ring system. For example, Figure a represents possible substitution in any of the positions shown in Figure b.

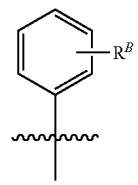

Figure a

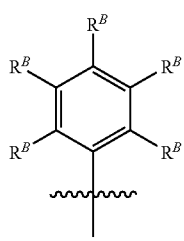

Figure b

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools, probes in biological assays, or CFTR correctors with improved therapeutic profile.

In one embodiment, the present invention provides a process for preparing Compound 1:

Compound 1

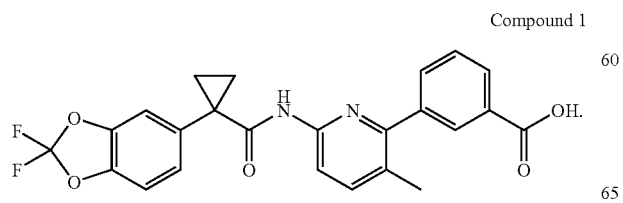

In some embodiments, the process for preparing Compound 1 comprises the steps of:

i) providing 2-bromo-3-methylpyridine (compound 2) and 3-(t-butoxycarbonyl)phenylboronic acid (compound 3),

2

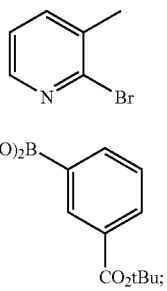

3

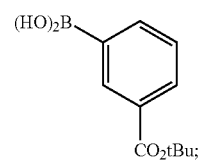

ii) cross coupling compound 2 and compound 3 in a biphasic mixture comprising water, a first organic solvent, a first base, and a transition metal catalyst to produce compound 4,

4

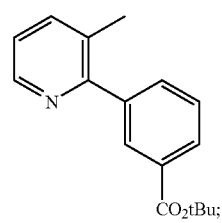

iii) oxidizing compound 4 to produce compound 5,

5

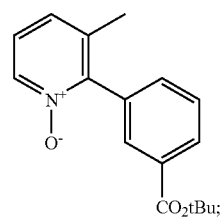

iv) adding an amine group to the 6 position of the pyridyl moiety to produce compound 6,

6

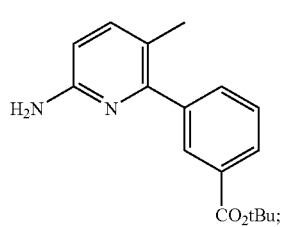

v) reacting compound 6 with compound 7,

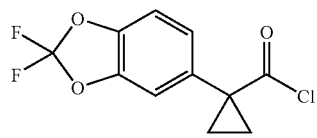
7 in a second organic solvent in the presence of a second base to produce compound 8,

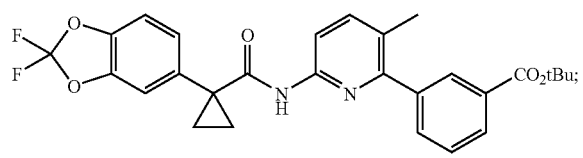
8 vi) de-esterifying compound 8 in a biphasic mixture comprising water, a third organic solvent, and a first acid to produce compound 9,

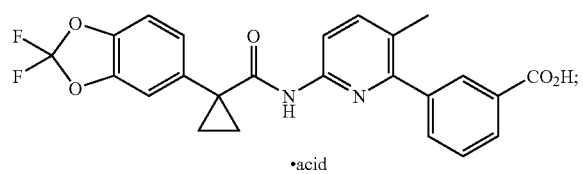
9
•acid vii) slurrying or dissolving compound 9 in an appropriate solvent for an effective amount of time to produce Compound 1.

In some embodiments, the first organic solvent is an aprotic solvent.

In some embodiments, the first organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, or dimethylsulfoxide.

In some embodiments, the first organic solvent is selected from acetonitrile, toluene, benzene, or xylenes. In some embodiments, the first organic solvent is toluene.

In other embodiments, the first organic solvent is a protic solvent. In some embodiments, the first organic solvent is selected from methanol, ethanol, or isopropanol.

In some embodiments, the first base is an inorganic base.

In some embodiments, the first base is selected from potassium carbonate, cesium carbonate, potassium phosphate, sodium carbonate, sodium phosphate, sodium hydroxide, potassium hydroxide or lithium hydroxide.

In some other embodiments, the first base is selected from potassium carbonate, cesium carbonate or potassium phosphate. In yet other embodiments, the first base is selected from potassium carbonate.

In some embodiments, the transition-metal catalyst is a palladium-based catalyst.

In some embodiments, the palladium-based catalyst is selected from palladium(II) acetate, Pd(dppf)Cl$_2$, tetrakis(triphenylphosphine)palladium(0) or tris(dibenzylideneacetone)dipalladium(0). In yet other embodiments, the palladium-based catalyst is Pd(dppf)Cl$_2$.

In some embodiments, the cross coupling reaction is run at between about 60° C. and about 100° C.

In other embodiments, the cross coupling reaction is run at between about 70° C. and about 90° C. In yet other embodiments, the cross coupling reaction is run at about 80° C.

In some embodiments, the oxidation reaction is carried out using a peroxide.

In some embodiments, the oxidation reaction is carried out using a peroxide selected from urea-hydrogen peroxide, peracetic acid, methyl ethyl ketone peroxide, sodium peroxide, hydrogen peroxide, potassium peroxide, lithium peroxide, barium peroxide, calcium peroxide, strontium peroxide, magnesium peroxide, zinc peroxide, cadmium peroxide, or mercury peroxide. In some embodiments the oxidation reaction is carried out using peracetic acid.

In some embodiments, the oxidation reaction is carried out in the presence of an anhydride.

In some embodiments, the oxidation reaction is carried out in the presence of an anhydride selected from acetic anhydride, phthalic anhydride, or maleic anhydride. In some embodiments, the oxidation reaction is carried out in the presence of phthalic anhydride.

In some embodiments, the oxidation reaction is run at between about 25° C. and about 65° C.

In some embodiments, the oxidation reaction is run at between about 35° C. and about 55° C. In yet other embodiments, the oxidation reaction is run at about 45° C.

In some embodiments, the amination reaction is carried out in the presence of a sulfonyl compound.

In some embodiments, the amination reaction is carried out in the presence of a sulfonyl compound selected from p-toluenesulfonyl chloride, methanesulfonic anhydride, methansulfonyl chloride, or p-toluenesulfonic anhydride. In some embodiments, the amination reaction is carried out in the presence of methanesulfonic anhydride.

In some embodiments, the amination reaction is carried out at ambient temperatures.

In some embodiments, the amination reagent used in the amination reaction is an alcohol amine.

In some embodiments, the amination reagent used in the amination reaction is an alcohol amine selected from methanolamine, ethanolamine, propanolamine, butanolamine, pentanolamine, or hexanolamine. In some embodiments, the amination reagent used in the amination reaction is ethanolamine.

In some embodiments, the second organic solvent is an aprotic solvent.

In some embodiments, the second organic solvent is an aprotic solvent selected from 1,2-dimethoxyethane, dioxane, acetonitrile, toluene, benzene, xylenes, methyl t-butyl ether, methylene chloride, chloroform, methyl ethyl ketone, methyl isobutyl ketone, acetone, N,N-dimethylformamide, N,N-dimethylacetamide, N-methylpyrrolidinone, or dimethylsulfoxide. In some embodiments, the second organic solvent is toluene.

In some embodiments, the second base is an organic base.

In some embodiments, the second base is an organic base selected from triethylamine, trimethylamine, methylamine, diethylamine, tripropylamine, ethylmethylamine, diethylmethylamine, or pyridine. In some embodiments, the second base is triethylamine.

In some embodiments, the reaction between compound 6 and compound 7 is carried out in the presence of a catalytic amine. In some embodiments, the reaction between compound 6 and compound 7 is carried out in the presence of a catalytic amount of dimethylaminopyridine.

In some embodiments, the third organic solvent is an aprotic solvent.

In some embodiments, the third organic solvent is an aprotic solvent selected from 1,2-dimethoxyethane, dioxane, acetonitrile, toluene, benzene, xylenes, methyl t-butyl ether, methylene chloride, chloroform, methyl ethyl ketone, methyl isobutyl ketone, acetone, N,N-dimethylformamide, N,N-dimethylacetamide, N-methylpyrrolidinone, or dimethylsulfoxide. In some embodiments, the third organic solvent is acetonitrile.

In some embodiments, the first acid is an inorganic acid.

In some embodiments, the first acid is an inorganic acid selected from hydrochloric, sulfuric, nitric, phosphoric, or boric acid. In some embodiments, the first acid is hydrochloric acid.

In some embodiments, the de-esterification reaction is run at between about 20° C. and about 60° C.

In other embodiments, the de-esterification reaction is run at between about 30° C. and about 50° C. In still other embodiments, the de-esterification reaction is run at about 40° C.

In some embodiments, the appropriate solvent is selected from water or an alcohol/water mixture. In some embodiments, the appropriate solvent is selected from water or an about 50% methanol/water mixture. In other embodiments, the appropriate solvent is water.

In some embodiments, the effective amount of time is between about 2 and about 24 hours.

In some embodiments, the effective amount of time is between about 2 and about 18 hours. In other embodiments, the effective amount of time is between about 2 and about 12 hours. In still other embodiments, the effective amount of time is between about 2 and about 6 hours.

In other embodiments, the process further comprises the step of filtering the slurry of Compound 1 or concentrating the solution of Compound 1 to effect recrystallization and filter the recrystallized Compound 1.

In other embodiments, Compound 1 is further purified by recrystallization from an organic solvent. Examples of organic solvents include, but are not limited to, toluene, cumene, anisole, 1-butanol, isopropyl acetate, butyl acetate, isobutyl acetate, methyl t-butyl ether, methyl isobutyl ketone, or 1-propanol/water (at various ratios). For example, in one embodiment, Compound 1 is dissolved in 1-butanol at about 75° C. until it is completely dissolved. Cooling down the solution to about 10° C. at a rate of about 0.2° C./min yields crystals of Compound 1 which may be isolated by filtration.

In other embodiments, the process for preparing Compound 1 comprises the step of:

i) reacting compound 6,

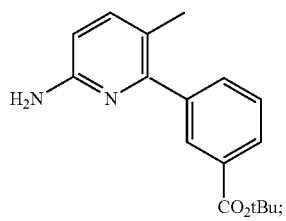

with compound 7,

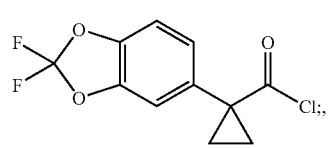

in a second organic solvent in the presence of a second base to produce compound 8,

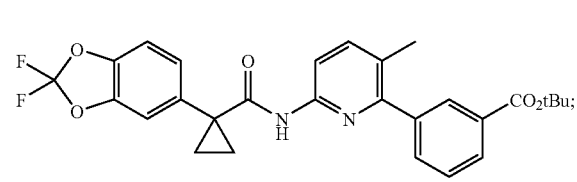

ii) de-esterifying compound 8 in a biphasic mixture comprising water, a third organic solvent, and a first acid to produce compound 9,

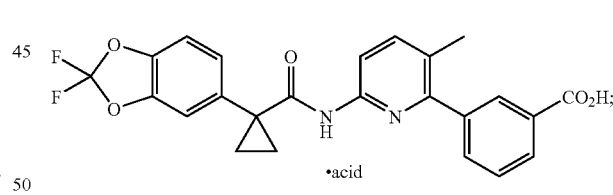

iii) slurrying or dissolving compound 9 in an appropriate solvent for an effective amount of time to produce Compound 1.

In some embodiments, the second organic solvent is an aprotic solvent.

In some embodiments, the second organic solvent is an aprotic solvent selected from 1,2-dimethoxyethane, dioxane, acetonitrile, toluene, benzene, xylenes, methyl t-butyl ether, methylene chloride, chloroform, methyl ethyl ketone, methyl isobutyl ketone, acetone, N,N-dimethylformamide, N,N-dimethylacetamide, N-methylpyrrolidinone, or dimethylsulfoxide. In some embodiments, the second organic solvent is toluene.

In some embodiments, the second base is an organic base.

In some embodiments, the second base is an organic base selected from triethylamine, trimethylamine, methylamine, diethylamine, tripropylamine, ethylmethylamine, diethylmethylamine, or pyridine. In some embodiments, the second base is triethylamine.

In some embodiments, the reaction between compound 6 and compound 7 is carried out in the presence of a catalytic amine. In some embodiments, the reaction is carried out in the presence of a catalytic amount of dimethylaminopyridine.

In some embodiments, the third organic solvent is an aprotic solvent.

In some embodiments, the third organic solvent is an aprotic solvent selected from 1,2-dimethoxyethane, dioxane, acetonitrile, toluene, benzene, xylenes, methyl t-butyl ether, methylene chloride, chloroform, methyl ethyl ketone, methyl isobutyl ketone, acetone, N,N-dimethylformamide, N,N-dimethylacetamide, N-methylpyrrolidinone, or dimethylsulfoxide. In some embodiments, the third organic solvent is acetonitrile.

In some embodiments, the first acid is an inorganic acid.

In some embodiments, the first acid is an inorganic acid selected from hydrochloric, sulfuric, nitric, phosphoric, or boric acid. In some embodiments, the first acid is hydrochloric acid.

In some embodiments, the de-esterification reaction is run at between about 20° C. and about 60° C.

In other embodiments, the de-esterification reaction is run at between about 30° C. and about 50° C. In still other embodiments, the de-esterification reaction is run at about 40° C.

In some embodiments, the appropriate solvent is selected from water or an alcohol/water mixture. In some embodiments, the appropriate solvent is selected from water or an about 50% methanol/water mixture. In other embodiments, the appropriate solvent is water.

In some embodiments, the effective amount of time is between about 2 and about 24 hours.

In some embodiments, the effective amount of time is between about 2 and about 18 hours. In other embodiments, the effective amount of time is between about 2 and about 12 hours. In still other embodiments, the effective amount of time is between about 2 and about 6 hours.

In other embodiments, the process further comprises the step of filtering the slurry of Compound 1 or concentrating the solution of Compound 1 to effect recrystallization and filter the recrystallized Compound 1.

In some embodiments, Compound 1 is further purified by recrystallization from an organic solvent. In other embodiments, Compound 1 is further purified by recrystallization from an organic solvent. Examples of organic solvents include, but are not limited to, toluene, cumene, anisole, 1-butanol, isopropyl acetate, butyl acetate, isobutyl acetate, methyl t-butyl ether, methyl isobutyl ketone, or 1-propanol/water (at various ratios). For example, in one embodiment, Compound 1 is dissolved in 1-butanol at about 75° C. until it is completely dissolved. Cooling down the solution to about 10° C. at a rate of about 0.2° C./min yields crystals of Compound 1 which may be isolated by filtration.

In another embodiment, the present invention provides a process for preparing a compound of formula I:

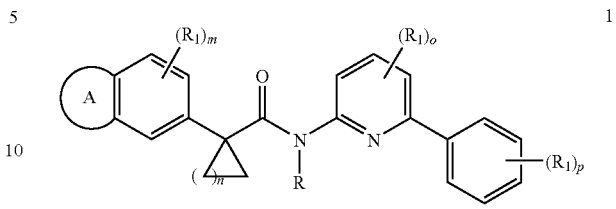

comprising the step of:
ia) reacting a compound of formula 6a:

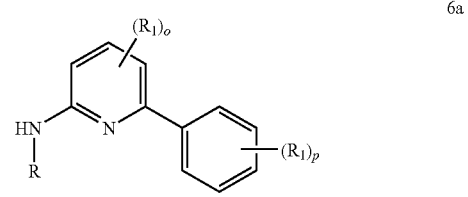

wherein,
R is H, $C_{1-6}$ aliphatic, aryl, aralkyl, heteroaryl, cycloalkyl, or heterocycloalkyl;
$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
$R^J$ is hydrogen or $C_{1-6}$ aliphatic;
o is an integer from 0 to 3 inclusive; and
p is an integer from 0 to 5 inclusive;
with a compound of formula 7a:

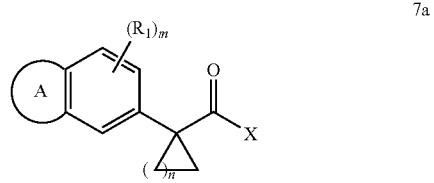

wherein,
A is a fused cycloalkyl, heterocycloalkyl, aryl, or heteroaryl ring;
$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
$R^J$ is hydrogen or $C_{1-6}$ aliphatic;
m is an integer from 0 to 3 inclusive;
n is an integer from 1 to 4 inclusive; and
X is a halo or OH;
in a second organic solvent in the presence of a second base.

In some embodiments, the second organic solvent is an aprotic solvent.

In some embodiments, the second organic solvent is an aprotic solvent selected from 1,2-dimethoxyethane, dioxane, acetonitrile, toluene, benzene, xylenes, methyl t-butyl ether, methylene chloride, chloroform, methyl ethyl ketone, methyl isobutyl ketone, acetone, N,N-dimethylformamide, N,N-dimethylacetamide, N-methylpyrrolidinone, or dimethylsulfoxide. In some embodiments, the second organic solvent is toluene.

In some embodiments, the second base is an organic base.

In some embodiments, the second base is an organic base selected from triethylamine, trimethylamine, methylamine, diethylamine, tripropylamine, ethylmethylamine, diethylmethylamine, or pyridine. In some embodiments, the second base is triethylamine.

In some embodiments, the reaction of compound 6a with compound 7a is carried out in the presence of a catalytic amine. In some embodiments, the reaction is carried out in the presence of a catalytic amount of dimethylaminopyridine.

In some embodiments, when $R_1$ on the phenyl ring in formula I is an ester, the process further comprises de-esterifying the compound in a biphasic mixture comprising water, a third organic solvent, and a first acid to give an acid salt.

In some embodiments, the third organic solvent is an aprotic solvent selected from 1,2-dimethoxyethane, dioxane, acetonitrile, toluene, benzene, xylenes, methyl t-butyl ether, methylene chloride, chloroform, methyl ethyl ketone, methyl isobutyl ketone, acetone, N,N-dimethylformamide, N,N-dimethylacetamide, N-methylpyrrolidinone, or dimethylsulfoxide. In some embodiments, the third organic solvent is acetonitrile.

In some embodiments, the first acid is an inorganic acid.

In some embodiments, the third acid is an inorganic acid selected from hydrochloric, sulfuric, nitric, phosphoric, or boric acid. In some embodiments, the first acid is hydrochloric acid.

In some embodiments, the de-esterification reaction is run at between about 20° C. and about 60° C.

In other embodiments, the de-esterification reaction is run at between about 30° C. and about 50° C. In still other embodiments, the de-esterification reaction is run at about 40° C.

In some embodiments, the acid salt can be converted to the free form, Form I, by slurrying or dissolving the acid salt in an appropriate solvent for an effective amount of time.

In some embodiments, the appropriate solvent is selected from water or an alcohol/water mixture. In some embodiments, the appropriate solvent is selected from water or an about 50% methanol/water mixture. In other embodiments, the appropriate solvent is water.

In some embodiments, the effective amount of time is between about 2 and about 24 hours.

In some embodiments, the effective amount of time is between about 2 and about 18 hours. In other embodiments, the effective amount of time is between about 2 and about 12 hours. In still other embodiments, the effective amount of time is between about 2 and about 6 hours.

In other embodiments, the process further comprises the step of filtering the slurry of the compound of formula I in Form I, or concentrating the solution of the compound of formula I in Form I to effect recrystallization and filtering the recrystallized compound of formula I in Form I.

In other embodiments, Compound 1 is further purified by recrystallization from an organic solvent. Examples of organic solvents include, but are not limited to, toluene, cumene, anisole, or 1-butanol. For example, in one embodiment, Compound 1 is dissolved in 1-butanol at about 75° C. until it is completely dissolved. Cooling down the solution to about 10° C. at a rate of about 0.2° C./min yields crystals of Compound 1 which may be isolated by filtration.

In another embodiment, the present invention provides a process for preparing a compound of formula 6a:

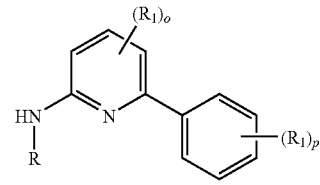

wherein,
R is H, $C_{1-6}$ aliphatic, aryl, aralkyl, heteroaryl, cycloalkyl, or heterocycloalkyl;
$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
$R^J$ is hydrogen or $C_{1-6}$ aliphatic;
o is an integer from 0 to 3 inclusive; and
p is an integer from 0 to 5 inclusive;
comprising the steps of:
 ib) providing compound 2a and compound 3a,

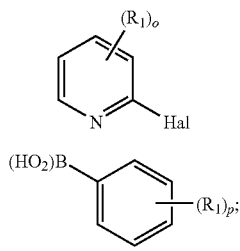

wherein,
$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
$R^J$ is hydrogen or $C_{1-6}$ aliphatic;
o is an integer from 0 to 4 inclusive; and
p is an integer from 0 to 5 inclusive;
 iib) cross coupling compound 2a and compound 3a in a biphasic mixture comprising water, a first organic solvent, a first base, and a transition metal catalyst to produce compound 4a,

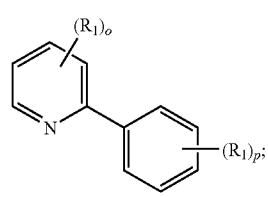

wherein, $R_1$, o, and p are as defined for compounds 2a and 3a above;

iiib) oxidizing compound 4a to produce compound 5a,

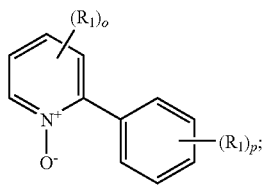

wherein, $R_1$, o, and p are as defined for compounds 2a and 3a above;

ivb) adding an amine group to the 6 position of the pyridyl moiety to produce compound 6a,

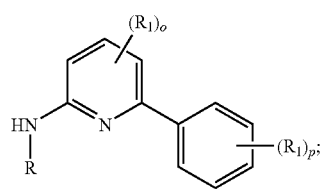

wherein,
R is H, $C_{1-6}$ aliphatic, aryl, aralkyl, heteroaryl, cycloalkyl, or heterocycloalkyl; and
$R_1$, o, and p are as defined for compounds 2a and 3a above.

In some embodiments, the first organic solvent is an aprotic solvent.

In some embodiments, the first organic solvent is selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, or dimethylsulfoxide.

In some embodiments, the first organic solvent is selected from acetonitrile, toluene, benzene, or xylenes. In some embodiments, the first organic solvent is toluene.

In other embodiments, the first organic solvent is a protic solvent. In some embodiments, the first organic solvent is selected from methanol, ethanol, or isopropanol.

In some embodiments, the first base is an inorganic base.

In some embodiments, the first base is selected from potassium carbonate, cesium carbonate, potassium phosphate, sodium carbonate, sodium phosphate, sodium hydroxide, potassium hydroxide or lithium hydroxide.

In some other embodiments, the first base is selected from potassium carbonate, cesium carbonate or potassium phosphate. In yet other embodiments, the first base is potassium carbonate.

In some embodiments, the transition-metal catalyst is a palladium-based catalyst.

In some embodiments, the palladium-based catalyst is selected from palladium(II) acetate, Pd(dppf)Cl$_2$, tetrakis(triphenylphosphine)palladium(0) or tris(dibenzylideneacetone)dipalladium(0). In yet other embodiments, the palladium-based catalyst is Pd(dppf)Cl$_2$.

In some embodiments, the cross coupling reaction is run at between about 60° C. and about 100° C.

In other embodiments, the cross coupling reaction is run at between about 70° C. and about 90° C. In yet other embodiments, the cross coupling reaction is run at about 80° C.

In some embodiments, the oxidation reaction is carried out using a peroxide.

In some embodiments, the oxidation reaction is carried out using a peroxide selected from urea-hydrogen peroxide, peracetic acid, methyl ethyl ketone peroxide, sodium peroxide, hydrogen peroxide, potassium peroxide, lithium peroxide, barium peroxide, calcium peroxide, strontium peroxide, magnesium peroxide, zinc peroxide, cadmium peroxide, or mercury peroxide. In some embodiments the oxidation reaction is carried out using peracetic acid.

In some embodiments, the oxidation reaction is carried out in the presence of an anhydride.

In some embodiments, the oxidation reaction is carried out in the presence of an anhydride selected from acetic anhydride, phthalic anhydride, or maleic anhydride. In some embodiments, the oxidation reaction is carried out in the presence of phthalic anhydride.

In some embodiments, the oxidation reaction is run at between about 25° C. and about 65° C.

In some embodiments, the oxidation reaction is run at between about 35° C. and about 55° C. In yet other embodiments, the oxidation reaction is run at about 45° C.

In some embodiments, the amination reaction is carried out in the presence of a sulfonyl compound.

In some embodiments, the amination reaction is carried out in the presence of a sulfonyl compound selected from p-toluenesulfonyl chloride, methanesulfonic anhydride, methansulfonyl chloride, or p-toluenesulfonic anhydride. In some embodiments, the amination reaction is carried out in the presence of methanesulfonic anhydride.

In some embodiments, the amination reaction is carried out at ambient temperatures.

In some embodiments, the amination reagent used in the amination reaction is an alcohol amine.

In some embodiments, the amination reagent used in the amination reaction is an alcohol amine selected from methanolamine, ethanolamine, propanolamine, butanolamine, pentanolamine, or hexanolamine. In some embodiments, the amination reagent used in the amination reaction is ethanolamine.

The present invention also provides a process for preparing a compound of formula 7a:

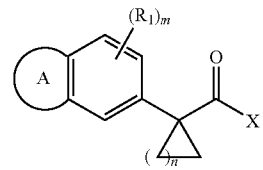

7a wherein,

A is a fused cycloalkyl, heterocycloalkyl, aryl, or heteroaryl ring;

$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —C(O)N($R^J$)$_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;

$R^J$ is hydrogen or $C_{1-6}$ aliphatic;

m is an integer from 0 to 3 inclusive;

n is an integer from 1 to 4 inclusive; and

X is a halide or OH;

comprising the steps of ic) reducing Compound 10a in a fourth organic solvent:

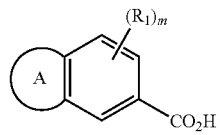
10a wherein,

A is a fused cycloalkyl, heterocycloalkyl, aryl, or heteroaryl ring;

$R_1$ is independently selected from —$R^J$, —$OR^J$, —$N(R^J)_2$, —$NO_2$, halogen, —CN, —$C_{1-4}$haloalkyl, —$C_{1-4}$haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;

$R^J$ is hydrogen or $C_{1-6}$ aliphatic; and m is an integer from 0 to 3 inclusive, with a reducing agent to produce Compound 11a:

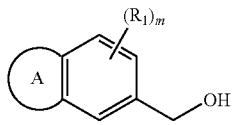
11a wherein, ring A, $R_1$, and m are as defined in Compound 10a above;

iic) reacting Compound 11a with a first halogenating agent in a fifth organic solvent to produce Compound 12a:

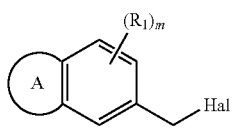
12a wherein, ring A, $R_1$, and m are as defined in Compound 10a above, and Hal is a halide;

iiic) reacting Compound 12a with a cyanide to produce Compound 13a:

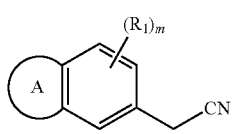
13a wherein, ring A, $R_1$, and m are as defined in Compound 10a above;

ivc) reacting Compound 13a with a compound of formula 13aa in the presence of a third base:

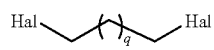
13aa wherein,

Hal is a halide; and q is an integer from 0 to 3 inclusive; to produce a compound of formula 14a:

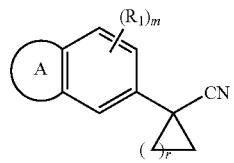
14a wherein, r is an integer from 1 to 4 inclusive; and ring A, $R_1$, and m are as defined in Compound 10a above;

vc) sequentially reacting Compound 14a with a hydroxide base and second acid to form Compound 15a, which is compound 7a when X=OH:

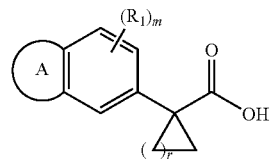
15a wherein, r, ring A, $R_1$, and m are as defined in Compound 14a above; and vic) reacting Compound 15a with a second halogenating agent in a sixth organic solvent to form Compound 16a, which is compound 7a when X=halide:

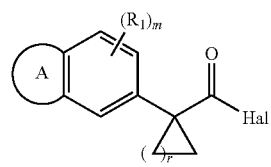
16a wherein,

Hal is halide; and r, ring A, $R_1$, and m are as defined in Compound 14a above.

In some embodiments, the fourth organic solvent is an aprotic solvent.

In some embodiments, the fourth organic solvent is an aprotic solvent selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, or dimethylsulfoxide.

In some embodiments, the fourth organic solvent is selected from acetonitrile, toluene, benzene, or xylenes. In some embodiments, the fourth organic solvent is toluene.

In some embodiments, the reducing agent is a hydride.

In some embodiments, the reducing agent is sodium hydride, lithium aluminum hydride, sodium borohydride, or sodium bis(2-methoxyethoxy)aluminum hydride. In some embodiments, the reducing agent is sodium bis(2-methoxyethoxy)aluminum hydride.

In some embodiments, the reducing reaction is run at between about 5° C. and about 50° C. In other embodiments, the reducing reaction is run at between about 15° C. and about 40° C.

In some embodiments, the fifth organic solvent is an aprotic solvent.

In some embodiments, the fifth organic solvent is an aprotic solvent selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, or dimethylsulfoxide.

In some embodiments, the fifth organic solvent is selected from acetonitrile, toluene, methyl t-butyl ether, benzene, or xylenes. In some embodiments, the fifth organic solvent is methyl t-butyl ether.

In some embodiments, the first halogenating agent is a thionyl halide. In other embodiments, the first halogenating agent is thionyl chloride.

In some embodiments, the reaction between Compound 11a and the first halogenating agent is run at between about 10° C. and about 35° C. In other embodiments, the halogenating reaction is run at between about 15° C. and about 30° C.

In some embodiments the cyanide is an alkali metal cyanide. In other embodiments, the cyanide is sodium cyanide.

In some embodiments, Compound 19 is dissolved in an organic solvent and added to a slurry of an alkali metal cyanide. In other embodiments, the organic solvent is DMSO.

In some embodiments, reaction of Compound 12a with a cyanide is run at between about 10° C. and about 60° C. In other embodiments, the reaction is run at between about 20° C. and about 50° C. In other embodiments, the reaction is run at between about 30° C. and about 40° C.

In some embodiments, the third base in step ivc) is an inorganic base.

In some embodiments, the third base is selected from potassium carbonate, cesium carbonate, potassium phosphate, sodium carbonate, sodium phosphate, sodium hydroxide, potassium hydroxide or lithium hydroxide.

In some embodiments, the third base is sodium hydroxide or potassium hydroxide. In some embodiments, the third base is potassium hydroxide.

In some embodiments, Compound 13aa is selected from dichloroethane, dichloropropane, dichlorobutane, dichloropentane, dibromoethane, dibromopropane, dibromobutane, dibromopentane, 1-bromo-2-chloroethane, 1-bromo-3-chloropropane, 1-bromo-4-chlorobutane, or 1-bromo-5-chloropentane.

In some embodiments, Compound 13aa is 1-bromo-2-chloroethane.

In some embodiments the reaction of Compound 13a with a compound of formula 13aa is run at between about 0° C. and about 90° C. In some embodiments the reaction is run at between about 60° C. and about 80° C. In some embodiments the reaction is run at about 70° C.

In some embodiments, the hydroxide base is sodium hydroxide, lithium hydroxide, or potassium hydroxide. In other embodiments, the hydroxide base is sodium hydroxide.

In some embodiments the second acid is an inorganic acid. In some embodiments, the second acid is selected from hydrochloric, sulfuric, nitric, phosphoric, or boric acid. In some embodiments, the second acid is hydrochloric acid.

In some embodiments, the sequential reaction of Compound 14a with hydroxide base and second acid is run at between about 70° C. and about 90° C. In some embodiments, the reaction is run at about 80° C.

In some embodiments, treating Compound 14a with a hydroxide base is done in the presence of a cosolvent. In other embodiments, the cosolvent is an alcohol. In other embodiments, the alcohol is ethanol.

In some embodiments, after treating Compound 14a with a hydroxide base, it is isolated before treatment with a second acid. In other embodiments, it is isolated as a different base than what was used to hydrolyze Compound 14a. In other embodiments, the different base used is cyclohexylamine to form the cyclohexylammonium salt.

In some embodiments, the sixth organic solvent is an aprotic solvent.

In some embodiments, the sixth organic solvent is an aprotic solvent selected from 1,2-dimethoxyethane, dioxane, acetonitrile, toluene, benzene, xylenes, methyl t-butyl ether, methyl ethyl ketone, methyl isobutyl ketone, acetone, N,N-dimethylformamide, N,N-dimethylacetamide, N-methylpyrrolidinone, or dimethylsulfoxide.

In some embodiments, the sixth organic solvent is selected from acetonitrile, toluene, benzene, or xylenes. In some embodiments, the sixth organic solvent is toluene.

In some embodiments, the second halogenating agent is a thionyl halide. In some embodiments the second halogenating agent is thionyl chloride.

In some embodiments, the reaction of Compound 15a with a second halogenating agent is run at between about 40° C. and about 80° C. In some embodiments, the reaction is run at between about 50° C. and about 70° C. In some embodiments, the reaction is run at about 70° C.

The present invention also provides a process for preparing Compound 1 from compound 9 below:

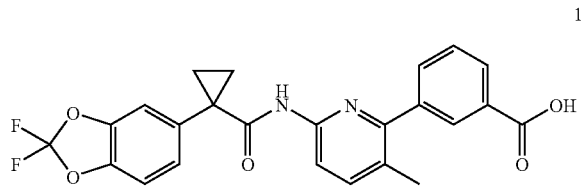

1

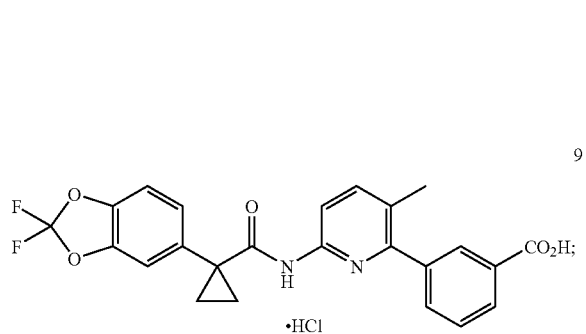

9 said process comprising the step of slurrying compound 9 in an appropriate solvent and stirring for an effective amount of time to produce Compound 1.

The present invention also provides a process for preparing Compound 1 from compound 9 below:

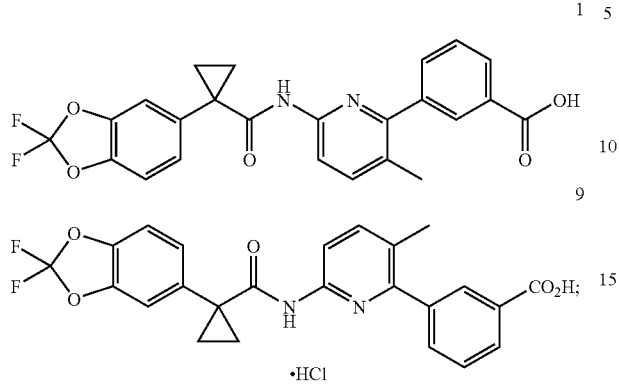

said process comprising the steps or slurrying compound 9, adding aqueous NaOH, and effecting recrystallization to produce Compound 1.

In some embodiments, recrystallization is achieved by adding concentrated HCl.

In some embodiments, the appropriate solvent is water or an about 50% methanol/water mixture. In some embodiments, the appropriate solvent is water.

In some embodiments, the effective amount of time is between about 2 hours and about 24 hours. In some embodiments, the effective amount of time is between about 2 hours and about 18 hours. In some embodiments, the effective amount of time is between about 2 hours and about 12 hours. In some embodiments, the effective amount of time is between about 2 hours and about 6 hours.

In some embodiments, the process further comprises the step of filtering the slurry of Compound 1.

In other embodiments, compound 9 is produced from compound 8 below:

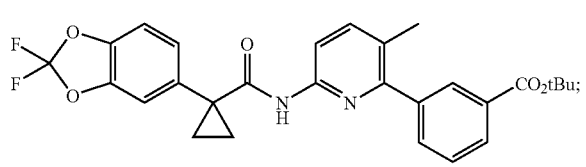

said process comprising the step of de-esterifying compound 8 in a biphasic mixture comprising water, a third organic solvent, and a first acid to produce compound 9.

In some embodiments, the third organic solvent is an aprotic solvent. In some embodiments, the third organic solvent is an aprotic solvent selected from 1,2-dimethoxyethane, dioxane, acetonitrile, toluene, benzene, xylenes, methyl t-butyl ether, methylene chloride, chloroform, methyl ethyl ketone, methyl isobutyl ketone, acetone, N,N-dimethylformamide, N,N-dimethylacetamide, N-methylpyrrolidinone, or dimethylsulfoxide. In some embodiments, the third organic solvent is acetonitrile.

In some embodiments, the first acid is an inorganic acid. In some embodiments, the first acid is selected from hydrochloric, sulfuric, nitric, phosphoric, or boric acid. In some embodiments, the first acid is hydrochloric acid.

In some embodiments, the de-esterification reaction is run at between about 20° C. and about 60° C. In some embodiments, the de-esterification reaction is run at between about 30° C. and about 50° C. In some embodiments, the de-esterification reaction is run at about 40° C.

In some embodiments, compound 8 is prepared from compound 6 and compound 7 below:

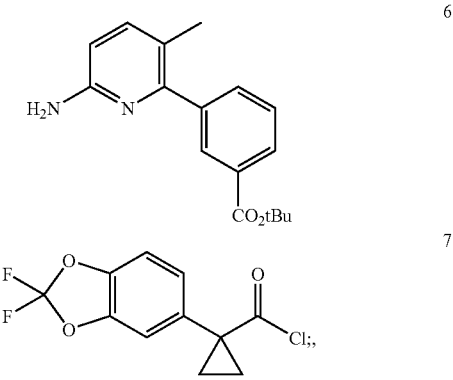

said process comprising the step reacting compound 6 with compound 7 in a second organic solvent in the presence of a second base to produce compound 8,

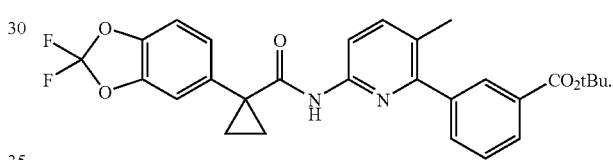

In some embodiments, the second organic solvent is an aprotic solvent. In some embodiments, the second organic solvent is an aprotic solvent selected from 1,2-dimethoxyethane, dioxane, acetonitrile, toluene, benzene, xylenes, methyl t-butyl ether, methylene chloride, chloroform, methyl ethyl ketone, methyl isobutyl ketone, acetone, N,N-dimethylformamide, N,N-dimethylacetamide, N-methylpyrrolidinone, or dimethylsulfoxide. In some embodiments, the second organic solvent is toluene.

In some embodiments, the second base is an organic base. In some embodiments, the second base is selected from triethylamine, trimethylamine, methylamine, diethylamine, tripropylamine, ethylmethylamine, diethylmethylamine, or pyridine. In some embodiments, the second base is triethylamine.

In some embodiments, the process is carried out in the presence of a catalytic amine. In some embodiments, the catalytic amine is dimethylaminopyridine.

In some embodiments, compound 6 is prepared from compound 4 below:

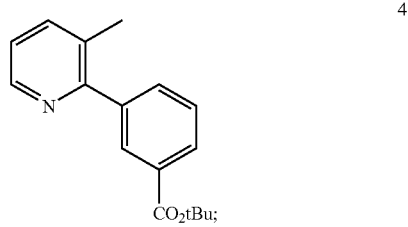

said process comprising the steps of:

oxidizing compound 4 to produce compound 5

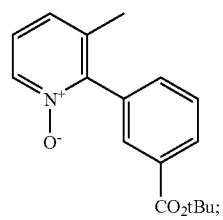

aminating compound 5 to add an amine group to the 6-position of the pyridyl moiety on compound 5 to produce compound 6,

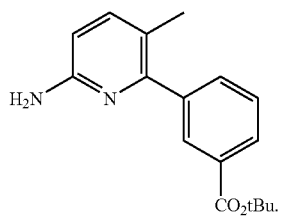

In some embodiments, the oxidation reaction is carried out using a peroxide. In some embodiments, the peroxide is selected from urea-hydrogen peroxide, peracetic acid, methyl ethyl ketone peroxide, sodium peroxide, hydrogen peroxide, potassium peroxide, lithium peroxide, barium peroxide, calcium peroxide, strontium peroxide, magnesium peroxide, zinc peroxide, cadmium peroxide, or mercury peroxide. In some embodiments, the peroxide is peracetic acid.

In some embodiments, the oxidation reaction is carried out in the presence of an anhydride. In some embodiments, the anhydride is selected from acetic anhydride, phthalic anhydride, or maleic anhydride. In some embodiments, the anhydride is phthalic anhydride.

In some embodiments, the oxidation reaction is run at between about 25° C. and about 65° C. In some embodiments, the oxidation reaction is run at between about 35° C. and about 55° C. In some embodiments, the oxidation reaction is run at about 45° C.

In some embodiments, the amination reaction is carried out in the presence of a sulfonyl compound. In some embodiments, the sulfonyl compound is selected from p-toluenesulfonyl chloride, methanesulfonic anhydride, methansulfonyl chloride, or p-toluenesulfonic anhydride. In some embodiments, the sulfonyl compound is methanesulfonic anhydride.

In some embodiments, the amination reaction is carried out at ambient temperature.

In some embodiments, the aminating reagent used in the amination reaction is an alcohol amine. In some embodiments, the alcohol amine is selected from methanolamine, ethanolamine, propanolamine, butanolamine, pentanolamine, or hexanolamine. In some embodiments, the alcohol amine is ethanolamine.

The present invention also provides a compound of formula 6b:

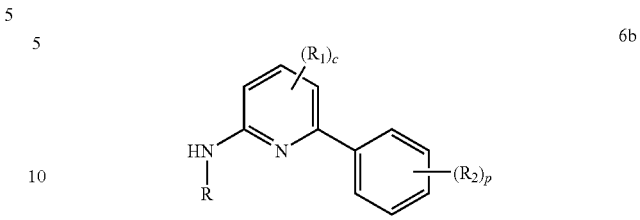

wherein,
R is H, $C_{1-6}$ aliphatic, aryl, aralkyl, heteroaryl, cycloalkyl, or heterocycloalkyl;
$R_1$ and $R_2$ are independently selected from —$R^J$, —$OR^J$, —$N(R^J)_2$, —$NO_2$, halogen, —CN, —$C_{1-4}$haloalkyl, —$C_{1-4}$ haloalkoxy, —$C(O)N(R^J)_2$, —$NR^JC(O)R^J$, —$SOR^J$, —$SO_2R^J$, —$SO_2N(R^J)_2$, —$NR^JSO_2R^J$, —$COR^J$, —$CO_2R^J$, —$NR^JSO_2N(R^J)_2$, —$COCOR^J$;
$R^J$ is hydrogen or $C_{1-6}$ aliphatic;
o is an integer from 0 to 3 inclusive; and
p is an integer from 0 to 5 inclusive.

In some embodiments, the present invention relates to a compound of formula 6b and the attendant definitions wherein R is H.

In some embodiments, the present invention relates to a compound of formula 6b and the attendant definitions wherein $R_1$ is $C_{1-6}$ aliphatic and o is 1.

In some embodiments, the present invention relates to a compound of formula 6b and the attendant definitions wherein $R_1$ is methyl and o is 1.

In some embodiments, the present invention relates to a compound of formula 6b and the attendant definitions wherein $R_2$ is —$CO_2R^J$ and p is 1.

In some embodiments, the present invention relates to a compound of formula 6b and the attendant definitions wherein $R_2$ is —$CO_2R^J$, $R^J$ is $C_{1-6}$ aliphatic, and p is 1.

In some embodiments, the present invention relates to the compound

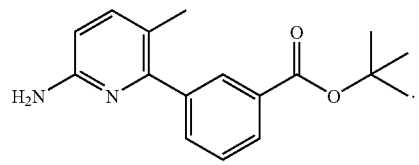

In some embodiments, Compound 1 may contain a radioactive isotope. In some embodiments, Compound 1 may contain a $^{14}C$ atom. In some embodiments, the amide carbonyl carbon of Compound 1 is a $^{14}C$ atom.

Methods of Preparing Compound 1.

Compound 1 is a free form of 3-(6-(1-(2,2-difluorobenzo[d][1,3]dioxol-5-yl)cyclopropanecarboxamido)-3-methylpyridin-2-yl)benzoic acid and, in one embodiment, is prepared from dispersing or dissolving a salt form, such as HCl, of 3-(6-(1-(2,2-difluorobenzo[d][1,3]dioxol-5-yl)cyclopropanecarboxamido)-3-methylpyridin-2-yl)benzoic acid in an appropriate solvent for an effective amount of time. In another embodiment, Form I is formed directly from 3-(6-(1-(2,2-difluorobenzo[d][1,3]dioxol-5-yl)cyclopropanecarboxamido)-3-methylpyridin-2-yl)-t-butylbenzoate and an appropriate acid, such as formic acid. In one embodiment, the HCl salt form of 3-(6-(1-(2,2-difluorobenzo[d][1,3]dioxol-5-yl)cyclopropanecarboxamido)-3-methylpyridin-2-yl)benzoic acid is the starting point and in one embodiment can be prepared by coupling an acid chloride moiety with an amine moiety according to Schemes 1-3.

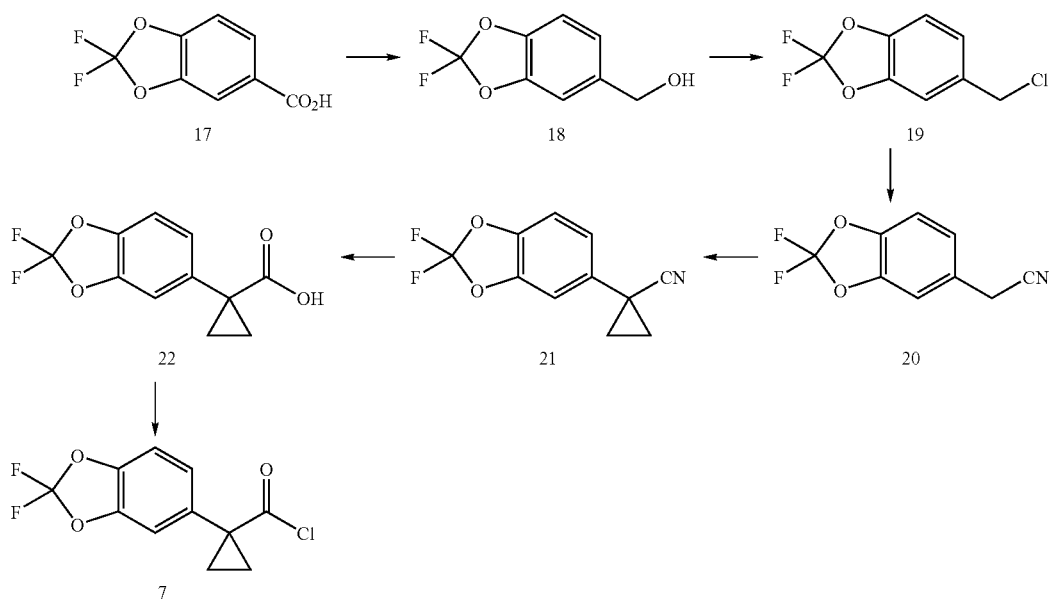

Scheme 1. Synthesis of the acid chloride moiety.

In Scheme 1, carboxylic acid 17 is reduced with a reducing agent in a suitable solvent (e.g. toluene) to produce alcohol 18. Treatment of Compound 18 with a chlorinating agent in a suitable solvent (e.g. methyl-t-butyl ether (MTBE)) produces Compound 19. A cyanide group displaces the chloride to yield compound 20. Reaction of compound 20 with a base and alkyl dihalide (e.g. 1-bromo-2-chloroethane) yields the spirocycloalkane compound 21. Hydrolization of the cyanide group gives the carboxylic acid 22 which is chlorinated to yield the acid halide 7.

In one embodiment, Compound 17 is commercially available. In one embodiment, the reducing agent is sodium bis(2-methoxyethoxy)aluminum hydride [or NaAlH$_2$(OCH$_2$CH$_2$OCH$_3$)$_2$], 65 wgt % solution in toluene, which is sold under the name Vitride® by Aldrich Chemicals.

In one embodiment, the chlorinating agent that converts Compound 18 to Compound 19 is thionyl chloride. In another embodiment, the thionyl chloride is added to Compound 18 while maintaining the temperature of the reaction mixture at 15° C. to 25° C. and then stirring for an additional hour continues at 30° C.

In one embodiment, the cyanide group of compound 20 results from reacting Compound 19 with sodium cyanide in a suitable solvent (e.g. DMSO). In another embodiment, the temperature of the reaction mixture is maintained at 30° C. to 40° C. while the sodium cyanide is being added.

In one embodiment, compound 20 is reacted with potassium hydroxide and an alkyl dihalide to yield the spirocyclic compound 21 in a suitable solvent (e.g. water). Although, a spirocyclic propane ring is depicted in Scheme 1, the process is easily adaptable to other spirocyclic rings by choosing the appropriate alkyl dihalide. For example, a spirocylic butane ring can be produced by reacting compound 20 with, for example, 1-bromo-3-chloropropane. It has been found that a mixed bromo and chloro dihalide works best on an economic scale as it is believed that the thermodynamics of the reaction are more favorable.

In one embodiment, compound 21 is hydrolized to the carboxylic acid compound 22 in the presence of water and a base (e.g. sodium hydroxide) in a suitable solvent (e.g. ethanol). Subsequent treatment with an acid such as hydrochloric acid yields compound 22. In another embodiment, compound 22 is worked up by reacting it with dicyclohexylamine (DCHA) to give the DCHA salt which is taken up in a suitable solvent (e.g. MTBE) and stirred with citric acid until the solids are dissolved. The MTBE layer is then washed with water and brine and a solvent swap with heptane followed by filtration gives compound 22.

In one embodiment, chlorination of compound 22 is carried out in a suitable solvent (e.g. toluene) with thionyl chloride to yield compound 7. In one embodiment, this step directly proceeds the coupling between compound 7 and compound 6 and is carried out in the same reaction vessel.

There are several non-limiting advantages to forming compound 7 according to Scheme 1 and the embodiments described above and elsewhere in the application. These advantages are apparent even more so when manufacturing compound 7 on an economic scale and include the following. Use of Vitride® over other reducing agents, such as lithium aluminum hydride, to reduce Compound 17 to Compound 18 allows controlled (manageable exothermic reaction and gas evolution) and safe addition of the reducing agent. Use of DMAP as a catalyst in the halogenating reaction of Compound 18 to Compound 19 as opposed to certain other bases such as DMF avoids formation of dimethylcarbamoyl chloride, a known carcinogen. Adding a solution of Compound 19 in an organic solvent such as DMSO to a slurry of the cyanide in an organic solvent such as DMSO controls the temperature of the exothermic reaction and minimizes the handling of the cyanide. Using ethanol as the cosolvent in hydrolyzing compound 21 to compound 22 results in a homogeneous reaction mixture making sampling and monitoring the reaction easier. Purification of compound 21 as the dicyclohexylammonium salt after the initial hydrolization eliminates chromatography of any of the intermediates.

Scheme 2. Synthesis of the amine moiety.

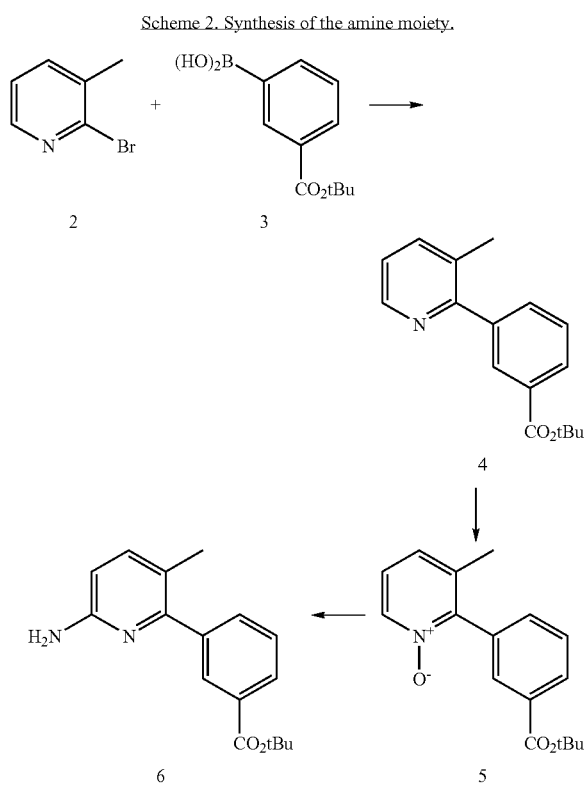

2-Bromo-3-methylpyridine (compound 2) is reacted with 3-(t-butoxycarbonyl)-phenylboronic acid (compound 3) in a suitable solvent (e.g. toluene) to yield the ester compound 4. The coupling reaction is catalyzed by a transition metal catalyst such as a palladium catalyst. Oxidation of compound 4 with a peroxide in a suitable solvent (e.g. a ethyl acetate -water mixture) yields compound 5. Amination of compound 5 with an aminating agent (e.g. an alcohol amine) yields compound 6.

In one embodiment, the palladium catalyst is Pd(dppf)Cl$_2$ which comprises a bidentate ferrocene ligand. In another embodiment, the catalyst is used only at 0.025 to 0.005 equivalents to compound 2. In another embodiment, the catalyst is used only at 0.020 to 0.010 equivalents to compound 2. In another embodiment, the catalyst is used only at 0.015 equivalents to compound 2.

In one embodiment, oxidation of compound 4 is carried out with urea-hydrogen peroxide or peracetic acid. Peracetic acid is preferred as it is more economically favorable to obtain and easier to isolate and dispose afterwards. In one embodiment, an anhydride is added portion-wise to the reaction mixture to maintain the temperature in the reaction vessel below 45° C. In one embodiment, the anhydride is phthalic anhydride and it is added in solid form. After completion of the anhydride addition, the mixture is heated to 45° C. and stirred for four hours before isolating compound 5.

In one embodiment, an amine group is added to compound 5 to yield compound 6 in a suitable solvent (e.g. pyridine-acetonitrile mixture). In one embodiment, amination occurs after compound 5 is first reacted with a sulfonic anhydride. In one embodiment, the sulfonic anhydride is methanesulfonic anhydride dissolved in acetonitrile and added over the course of 50 minutes to compound 5 dissolved in pyridine. In another embodiment, the temperature is maintained below 75° C. during addition. In another embodiment, the amination agent is ethanolamine. In another embodiment, the amount of ethanolamine is 10 equivalents relative to compound 5.

There are several non-limiting advantages to forming compound 6 according to Scheme 2 and the embodiments described above and elsewhere in the application. These advantages are apparent even more so when manufacturing compound 6 on an economic scale and include the following. Increasing the concentration of potassium carbonate in the coupling reaction of compounds 2 and 3 to form compound 4 reduces the level of boronic acid homo-coupling. The level of boronic acid homo-coupling is also reduced by adding the transition metal catalyst last to the reaction mixture after heating under N$_2$. Extracting compound 4 with aqueous MsOH eliminates the need for chromatographic purification. Using peracetic acid as the oxidizing agent when converting compound 4 to compound 5 is more economical than other oxidizing agents and results in more manageable by-products. Use of Ms$_2$O instead of other similar reagents, such as p-toluenesulfonyl chloride, in converting compound 5 to compound 6 eliminates formation of chloro impurities. Addition of water at the completion of the reaction crystallizes compound 6 directly from the reaction mixture improving yield and facilitating isolation.

Scheme 3. Formation of an acid salt of 3-(6-(1-(2,2-difluorobenzo[d][1,3]dioxol-5-yl)cyclopropanecarboxamido)-3-methylpyridin-2-yl)benzoic acid.

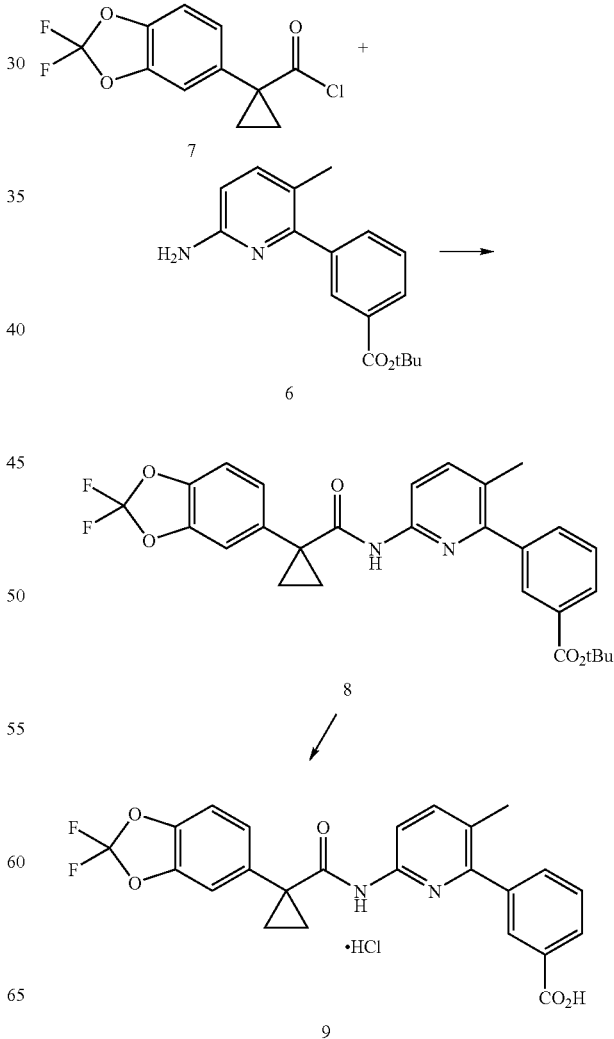

An acid-base reaction between compound 7 and compound 6 in a suitable solvent (e.g. toluene) yields the ester compound 8. De-esterification of compound 8 with an acid (hydrochloric acid shown) yields compound 9 which is the precursor to Compound 1.

In one embodiment, the acid chloride compound 7 is prepared from compound 22 as depicted in Scheme 1 in the same reaction vessel and is not isolated. In another embodiment, the acid-based reaction is carried out in the presence of a base such as triethylamine (TEA) and a catalytic amount of a second base such as dimethylaminopyridine (DMAP). In one embodiment, the amount of TEA is 3 equivalents relative to compound 6. In another embodiment, the amount of DMAP is 0.02 equivalents relative to compound 6. In one embodiment, after a reaction time of two hours, water is added to the mixture and stirred for an additional 30 minutes. The organic phase is separated and compound 9 is isolated by adding a suitable solvent (e.g. acetonitrile) and distilling off the reaction solvent (e.g. t). Compound 9 is collected by filtration.

Using compound 9, for example, as a starting point, Compound 1 can be formed in high yields by dispersing or dissolving compound 9 in an appropriate solvent for an effective amount of time. Other salt forms of 3-(6-(1-(2,2-difluorobenzo[d][1,3]dioxol-5-yl)cyclopropanecarboxamido)-3-methylpyridin-2-yl)benzoic acid may be used such as, for example, other mineral or organic acid forms. The other salt forms result from hydrolysis of the t-butyl ester with the corresponding acid. Other acids/salt forms include nitric, sulfuric, phosphoric, boric, acetic, benzoic, malonic, and the like. Compound 9 may or may not be soluble depending upon the solvent used, but lack of solubility does not hinder formation of Compound 1. For example, in one embodiment, the appropriate solvent may be water or an alcohol/water mixture such as an about 50% methanol/water mixture, even though compound 9 is only sparingly soluble in water. In one embodiment, the appropriate solvent is water.

The effective amount of time for formation of Compound 1 from the compound 9 can be any time between 2 to 24 hours or greater. Generally, greater than 24 hours is not needed to obtain high yields (~98%), but certain solvents may require greater amounts of time. It is also recognized that the amount of time needed is inversely proportional to the temperature. That is, the higher the temperature the less time needed to affect dissociation of HCl to form Compound 1. When the solvent is water, stirring the dispersion for approximately 24 hours at room temperature gives Compound 1 in an approximately 98% yield. If a solution of the compound 9 is desired for process purposes, an elevated temperature and organic solvent may be used. After stirring the solution for an effective amount of time at the elevated temperature, recrystallization upon cooling yields substantially pure forms of Compound 1. In one embodiment, substantially pure refers to greater than 90% purity. In another embodiment, substantially pure refers to greater than 95% purity. In another embodiment, substantially pure refers to greater than 98% purity. In another embodiment, substantially pure refers to greater than 99% purity. The temperature selected depends in part on the solvent used and is well within the capabilities of someone of ordinary skill in the art to determine. In one embodiment, the temperature is between room temperature and 80° C. In another embodiment, the temperature is between room temperature and 40° C. In another embodiment, the temperature is between 40° C. and 60° C. In another embodiment, the temperature is between 60° C. and 80° C.

In some embodiments, Compound 1 may be further purified by recrystallization from an organic solvent. Examples of organic solvents include, but are not limited to, toluene, cumene, anisole, 1-butanol, isopropylacetate, butyl acetate, isobutyl acetate, methyl t-butyl ether, methyl isobutyl ketone, or 1-propanol/water (at various ratios). Temperature may be used as described above. For example, in one embodiment, Compound 1 is dissolved in 1-butanol at 75° C. until it is completely dissolved. Cooling down the solution to 10° C. at a rate of 0.2° C./min yields crystals of Compound 1 which may be isolated by filtration.

There are several non-limiting advantages to forming compound 9 according to Scheme 3 and the embodiments described above and elsewhere in the application. These advantages are apparent even more so when manufacturing compound 9 on an economic scale and include the following. Crystallizing compound 8 after reacting compound 7 with compound 6 eliminates chromatographic purification. Direct crystallization of compound 9 after treating compound 8 with an acid versus deprotection with another acid, such as trifluoroacetic acid, concentration, and exchange with the desired acid, such as HCl, eliminates steps and improves yields.

In some embodiments, Compound 1 may comprise a radioactive isotope. In some embodiments, the radioactive isotope is $^{14}C$. In some embodiments, the amide carbonyl carbon of Compound 1 is $^{14}C$. The $^{14}C$ is introduced at this position by reacting compound 19 with a radiolabeled cyanide as depicted in Scheme 4.

Scheme 4. Introduction of a radioactive isotope into Compound 1.

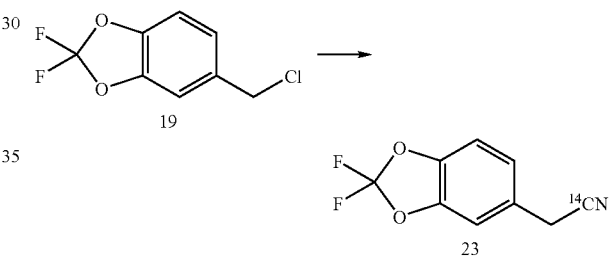

In one embodiment, the radiolabeled cyanide group of compound 23 results from reacting Compound 19 with radiolabeled sodium cyanide in a suitable solvent (e.g. DMSO). In another embodiment, the temperature of the reaction mixture is maintained at 30° C. to 40° C. while the sodium cyanide is being added. Compound 23 may then be further reacted according to Schemes 1-3 to produce radiolabeled Compound 1.

Characterization of Compound 1

Compound 1 exists as the substantially free form of 3-(6-(1-(2,2-difluorobenzo[d][1,3]dioxol-5-yl)cyclopropanecarboxamido)-3-methylpyridin-2-yl)benzoic acid, Form I, as characterized herein by X-ray powder diffraction, differential scanning calorimetry (DSC), thermogravimetric analysis (TGA), and $^{1}HNMR$ spectroscopy.

In one embodiment, Compound 1 is characterized by one or more peaks at 15.2 to 15.6 degrees, 16.1 to 16.5 degrees, and 14.3 to 14.7 degrees in an X-ray powder diffraction obtained using Cu K alpha radiation. In another embodiment, Compound 1 is characterized by one or more peaks at 15.4, 16.3, and 14.5 degrees. In another embodiment, Compound 1 is further characterized by a peak at 14.6 to 15.0 degrees. In another embodiment, Compound 1 is further characterized by a peak at 14.8 degrees. In another embodiment, Compound 1 is further characterized by a peak at 17.6 to 18.0 degrees. In another embodiment, Compound 1 is further characterized by a peak at 17.8 degrees. In another embodiment, Compound 1 is further characterized by a peak at 16.4 to 16.8 degrees. In another embodiment, Compound 1 is further characterized by a peak at 16.4 to 16.8 degrees. In another embodiment, Compound 1 is further characterized by a peak at 16.6 degrees. In another embodiment, Compound 1 is further characterized by a peak at 7.6 to 8.0 degrees. In another embodiment, Compound 1 is further characterized by a peak at 7.8 degrees. In another embodiment, Compound 1 is further characterized by a peak at 25.8 to 26.2 degrees. In another embodiment, Compound 1 is further characterized by a peak at 26.0 degrees. In another embodiment, Compound 1 is further characterized by a peak at 21.4 to 21.8 degrees. In another embodiment, Compound 1 is further characterized by a peak at 21.6 degrees. In another embodiment, Compound 1 is further characterized by a peak at 23.1 to 23.5 degrees. In another embodiment, Compound 1 is further characterized by a peak at 23.3 degrees.

In some embodiments, Compound 1 is characterized by a diffraction pattern substantially similar to that of FIG. 1.

Figure 2:
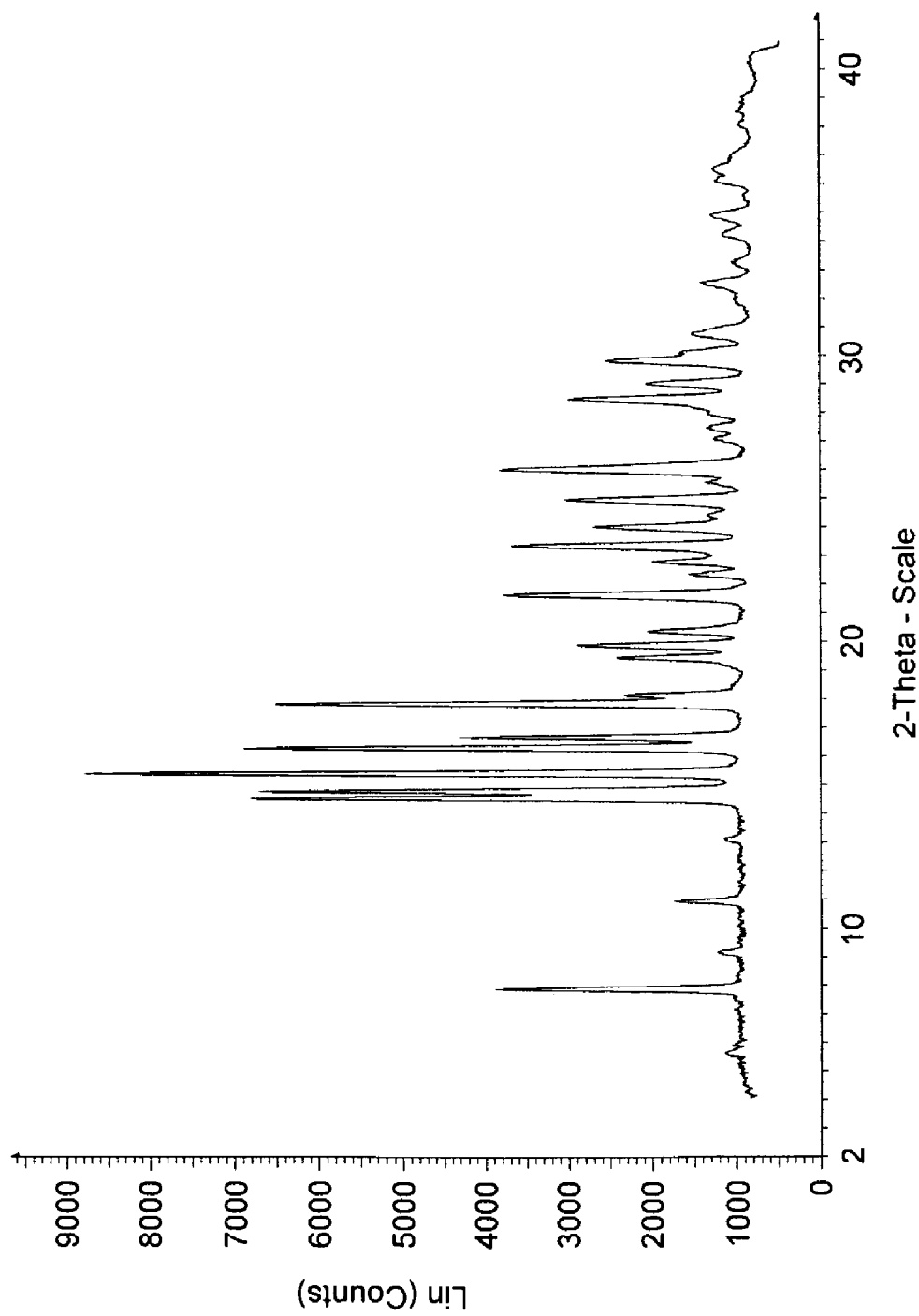
FIG. 2 is an actual X-ray powder diffraction pattern of Compound 1 in Form I.

In some embodiments, Compound 1 is characterized by a diffraction pattern substantially similar to that of FIG. 2.

In another embodiment, Compound 1 has a monoclinic crystal system, a $P2_1/n$ space group, and the following unit cell dimensions: a=4.9626 (7) Å; b=12.2994 (18) Å; c=33.075 (4) Å; α=90°; β=93.938 (9)°; and γ=90°.

Figure 4:
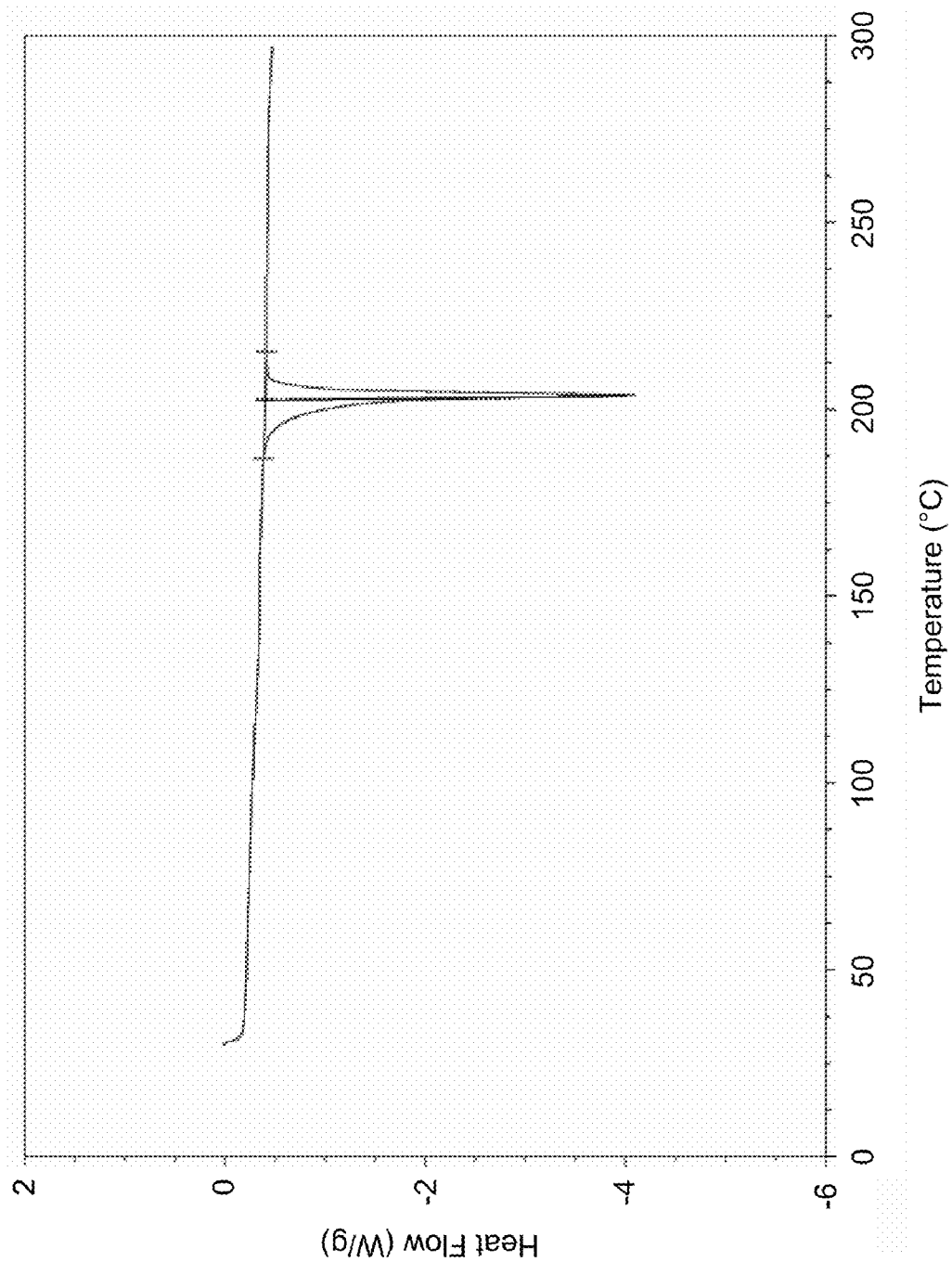
FIG. 4 is a differential scanning calorimetry (DSC) trace of Compound 1 in Form I.
Figure 5:
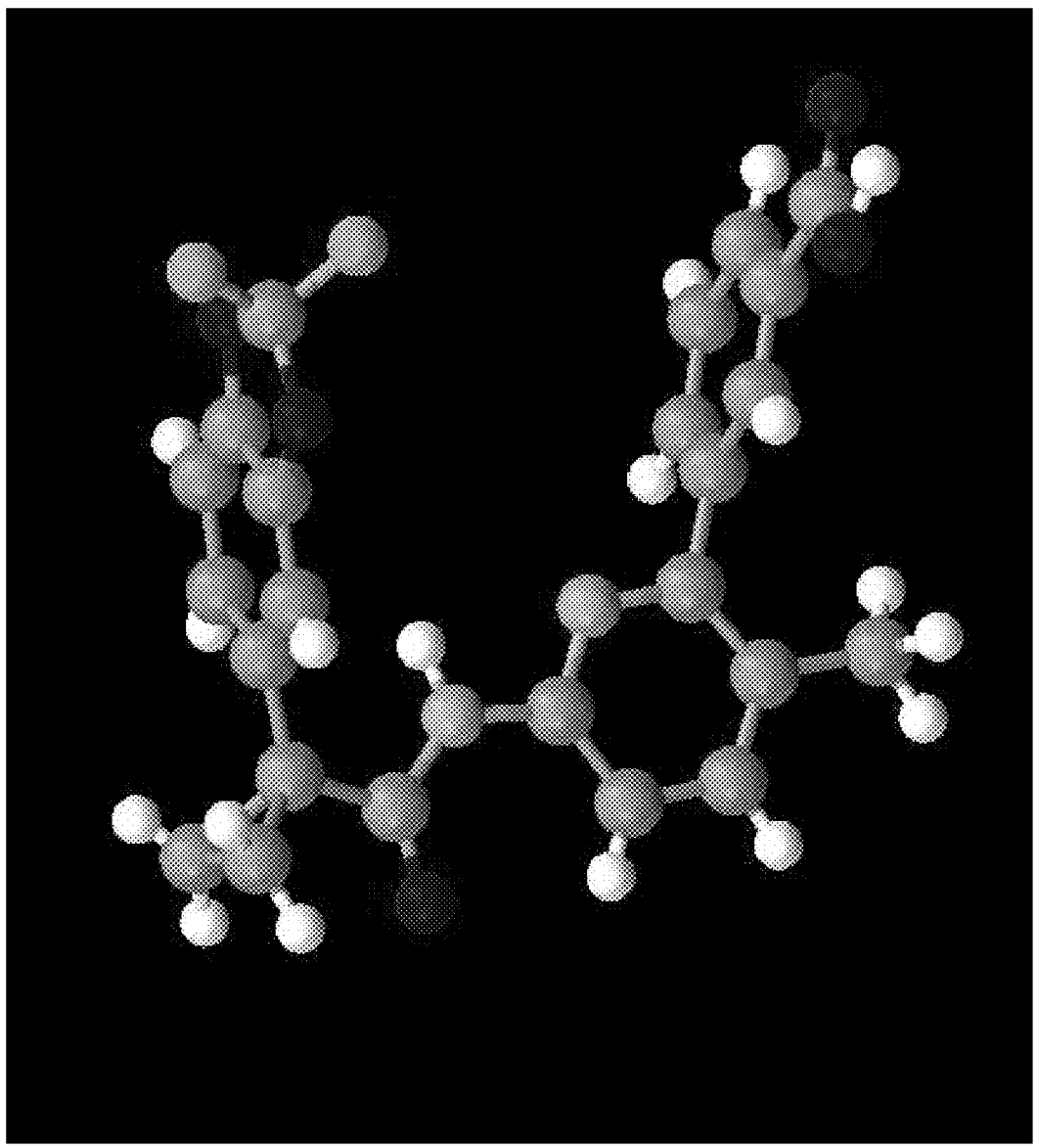
FIG. 5 is a conformational picture of Compound 1 in Form I based on single crystal X-ray analysis.

In another embodiment, Compound 1 is characterized by the DSC trace shown in FIG. 4.

Figure 8:
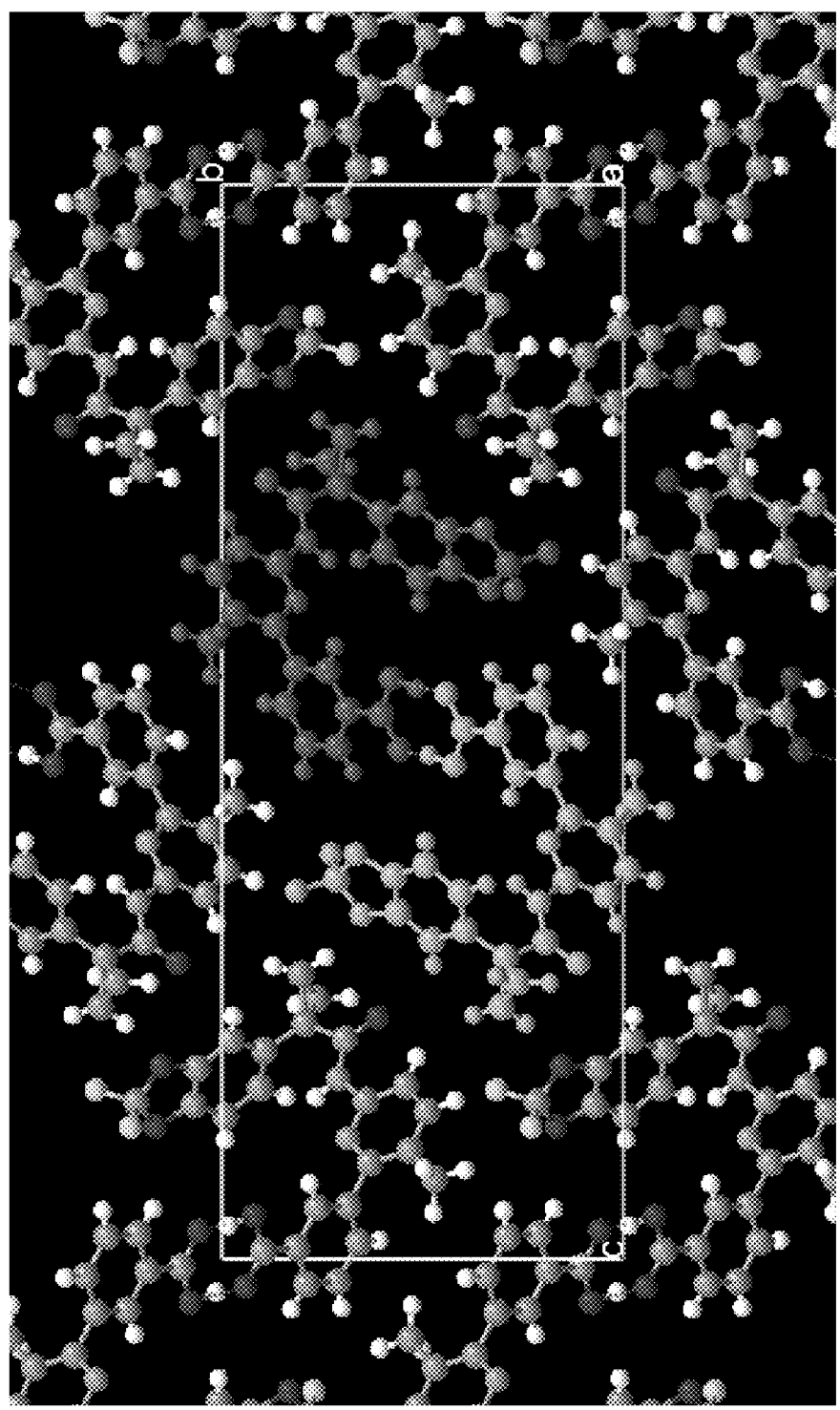
FIG. 8 is conformational picture of Compound 1 in Form I based on single crystal X-ray analysis showing a different view (down a).
Figure 9:
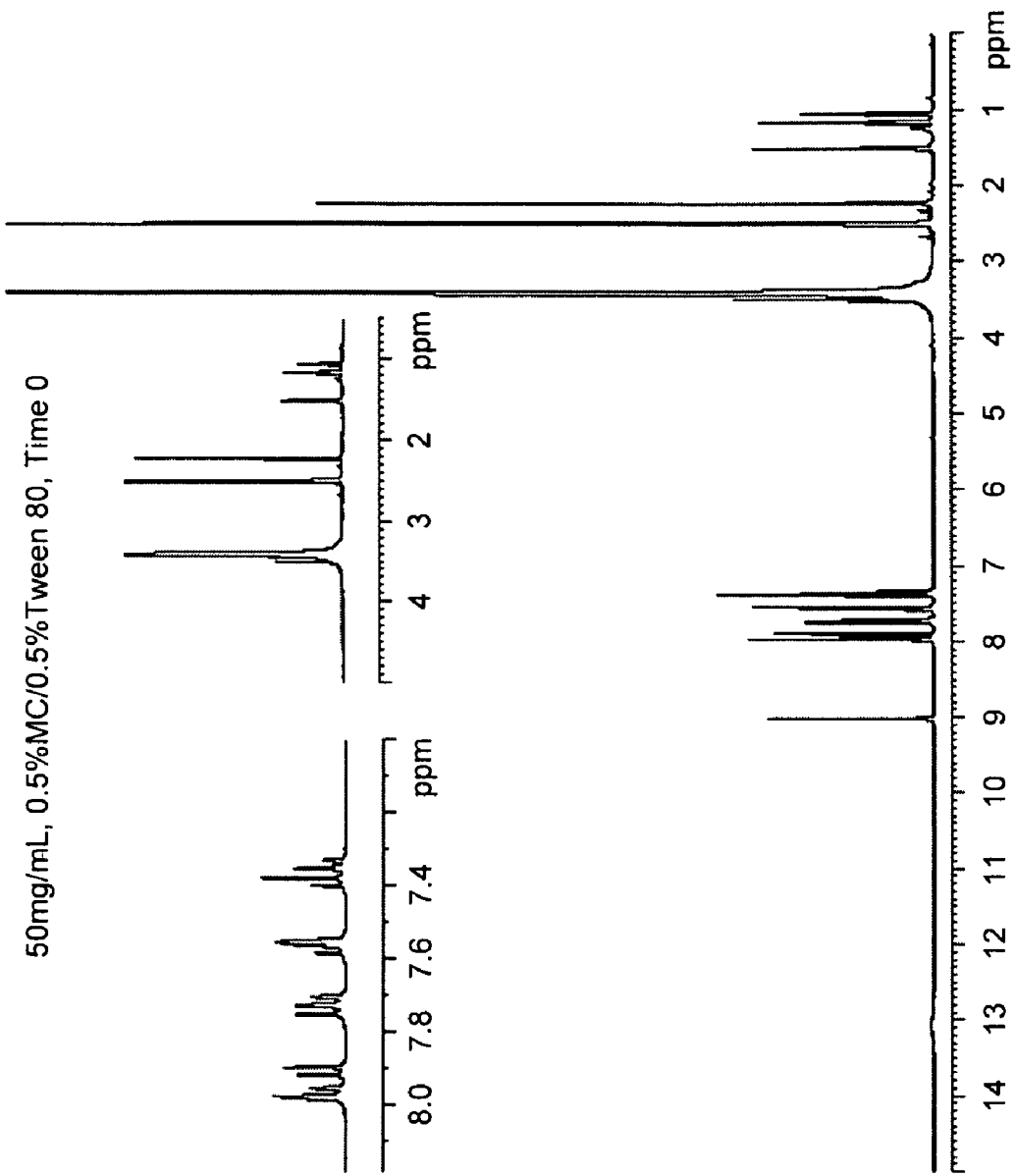
FIG. 9 is an $^1$HNMR analysis of Compound 1 in Form I in a 50 mg/mL, 0.5 methyl cellulose-polysorbate 80 suspension at T(0).
Figure 10:
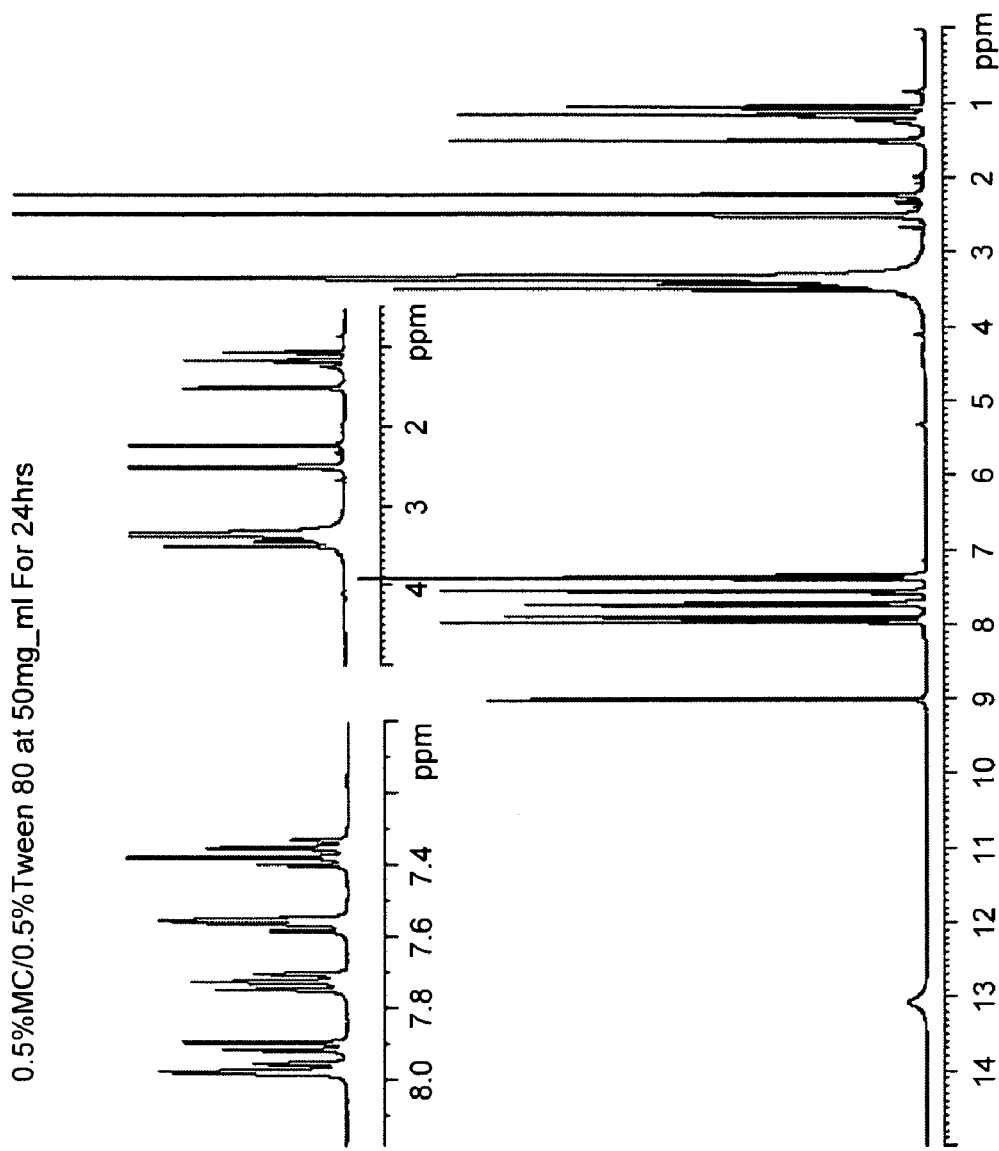
FIG. 10 is an $^1$HNMR analysis of Compound 1 in Form I in a 50 mg/mL, 0.5 methyl cellulose-polysorbate 80 suspension stored at room temperature for 24 hours.

In another embodiment, Compound 1 is characterized by the $^1$HNMR spectra of Compound 1 shown in FIGS. 8-10.

In order that the invention described herein may be more fully understood, the following examples are set forth. It should be understood that these examples are for illustrative purposes only and are not to be construed as limiting this invention in any manner.

EXAMPLES

Methods & Materials

Differential Scanning Calorimetry (DSC)

The Differential scanning calorimetry (DSC) data of Compound 1 were collected using a DSC Q100 V9.6 Build 290 (TA Instruments, New Castle, Del.). Temperature was calibrated with indium and heat capacity was calibrated with sapphire. Samples of 3-6 mg were weighed into aluminum pans that were crimped using lids with 1 pin hole. The samples were scanned from 25° C. to 350° C. at a heating rate of 1.0° C./min and with a nitrogen gas purge of 50 ml/min. Data were collected by Thermal Advantage Q Series™ version 2.2.0.248 software and analyzed by Universal Analysis software version 4.1D (TA Instruments, New Castle, Del.). The reported numbers represent single analyses.

XRPD (X-Ray Powder Diffraction)

The X-Ray diffraction (XRD) data of Form 1 were collected on a Bruker D8 DISCOVER powder diffractometer with HI-STAR 2-dimensional detector and a flat graphite monochromator. Cu sealed tube with Kα radiation was used at 40 kV, 35 mA. The samples were placed on zero-background silicon wafers at 25° C. For each sample, two data frames were collected at 120 seconds each at 2 different $\theta_2$ angles: 8° and 26°. The data were integrated with GADDS software and merged with DIFFRACT$^{plus}$EVA software. Uncertainties for the reported peak positions are ±0.2 degrees.

Vitride® (sodium bis(2-methoxyethoxy)aluminum hydride [or $NaAlH_2(OCH_2CH_2OCH_3)_2$], 65 wgt % solution in toluene) was purchased from Aldrich Chemicals.

2,2-Difluoro-1,3-benzodioxole-5-carboxylic acid was purchased from Saltigo (an affiliate of the Lanxess Corporation).

Anywhere in the present application where a name of a compound may not correctly describe the structure of the compound, the structure supersedes the name and governs.

Synthesis of 3-(6-(1-(2,2-difluorobenzo[d][1,3]dioxol-5-yl)cyclopropanecarboxamido)-3-methylpyridin-2-yl)benzoic acid.HCl Acid Chloride Moiety Synthesis of (2,2-difluoro-1,3-benzodioxol-5-yl)-methanol (Compound 18)

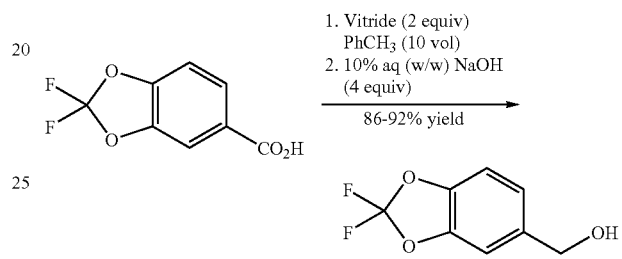

Commercially available 2,2-difluoro-1,3-benzodioxole-5-carboxylic acid (1.0 eq) is slurried in toluene (10 vol). Vitride® (2 eq) is added via addition funnel at a rate to maintain the temperature at 15-25° C. At the end of addition the temperature is increased to 40° C. for 2 h then 10% (w/w) aq. NaOH (4.0 eq) is carefully added via addition funnel maintaining the temperature at 40-50° C. After stirring for an additional 30 minutes, the layers are allowed to separate at 40° C. The organic phase is cooled to 20° C. then washed with water (2×1.5 vol), dried ($Na_2SO_4$), filtered, and concentrated to afford crude Compound 18 that is used directly in the next step.

Synthesis of 5-chloromethyl-2,2-difluoro-1,3-benzodioxole (Compound 19)

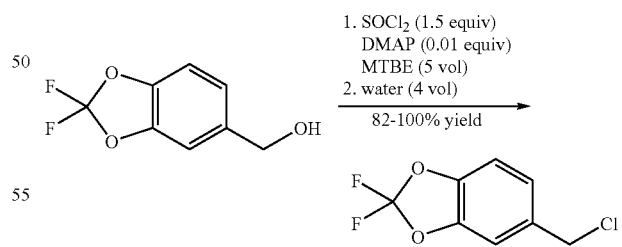

Compound 18 (1.0 eq) is dissolved in MTBE (5 vol). A catalytic amount of DMAP (1 mol %) is added and $SOCl_2$ (1.2 eq) is added via addition funnel. The $SOCl_2$ is added at a rate to maintain the temperature in the reactor at 15-25° C. The temperature is increased to 30° C. for 1 hour then cooled to 20° C. then water (4 vol) is added via addition funnel maintaining the temperature at less than 30° C. After stirring for an additional 30 minutes, the layers are allowed to separate. The organic layer is stirred and 10% (w/v) aq. NaOH (4.4 vol) is added. After stirring for 15 to 20 minutes, the layers are allowed to separate. The organic phase is then dried (Na$_2$SO$_4$), filtered, and concentrated to afford crude Compound 19 that is used directly in the next step.

Synthesis of
(2,2-difluoro-1,3-benzodioxol-5-yl)-acetonitrile
(Compound 20)

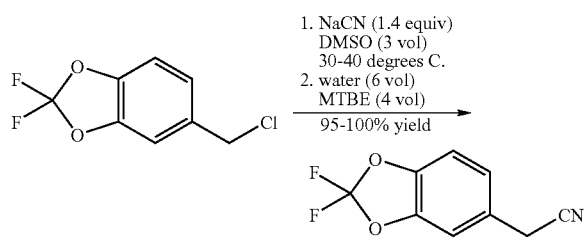

A solution of Compound 19 (1 eq) in DMSO (1.25 vol) is added to a slurry of NaCN (1.4 eq) in DMSO (3 vol) maintaining the temperature between 30-40° C. The mixture is stirred for 1 hour then water (6 vol) is added followed by MTBE (4 vol). After stirring for 30 min, the layers are separated. The aqueous layer is extracted with MTBE (1.8 vol). The combined organic layers are washed with water (1.8 vol), dried (Na$_2$SO$_4$), filtered, and concentrated to afford crude compound 20 (95%) that is used directly in the next step.

Synthesis of (2,2-difluoro-1,3-benzodioxol-5-yl)-cyclopropanecarbonitrile (Compound 21)

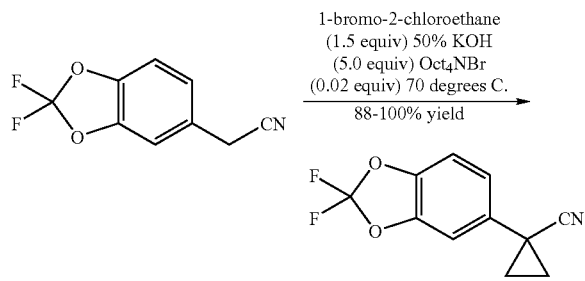

A mixture of compound 20 (1.0 eq), 50 wt % aqueous KOH (5.0 eq) 1-bromo-2-chloroethane (1.5 eq), and Oct$_4$NBr (0.02 eq) is heated at 70° C. for 1 h. The reaction mixture is cooled then worked up with MTBE and water. The organic phase is washed with water and brine then the solvent is removed to afford compound 21.

Synthesis of 1-(2,2-difluoro-1,3-benzodioxol-5-yl)-cyclopropanecarboxylic Acid (Compound 22)

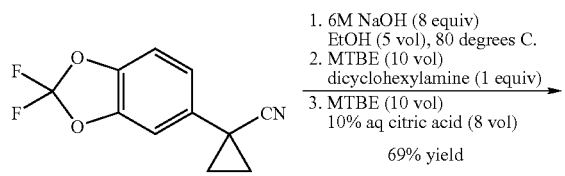

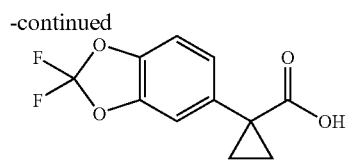

Compound 21 is hydrolyzed using 6 M NaOH (8 equiv) in ethanol (5 vol) at 80° C. overnight. The mixture is cooled to room temperature and ethanol is evaporated under vacuum. The residue is taken into water and MTBE, 1 M HCl was added and the layers are separated. The MTBE layer was then treated with dicyclohexylamine (0.97 equiv). The slurry is cooled to 0° C., filtered and washed with heptane to give the corresponding DCHA salt. The salt is taken into MTBE and 10% citric acid and stirred until all solids dissolve. The layers are separated and the MTBE layer was washed with water and brine. Solvent swap to heptane followed by filtration gives compound 22 after drying in a vacuum oven at 50° C. overnight.

Synthesis of 1-(2,2-difluoro-1,3-benzodioxol-5-yl)-cyclopropanecarbonyl Chloride (Compound 7)

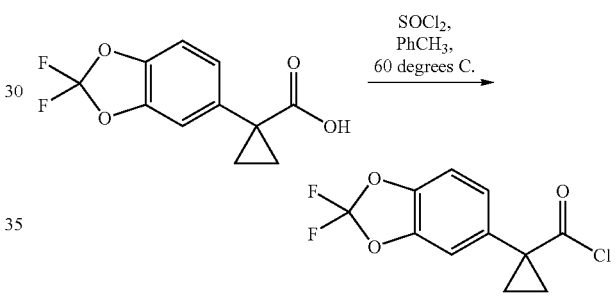

Compound 22 (1.2 eq) is slurried in toluene (2.5 vol) and the mixture heated to 60° C. SOCl$_2$ (1.4 eq) is added via addition funnel. The toluene and SOCl$_2$ are distilled from the reaction mixture after 30 minutes. Additional toluene (2.5 vol) is added and distilled again.

Synthesis of $^{14}$C-(2,2-difluoro-1,3-benzodioxol-5-yl)-acetonitrile (Compound 23)

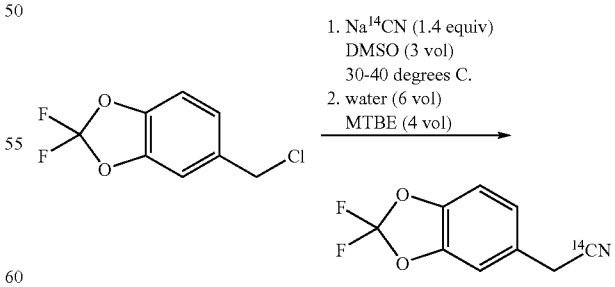

A solution of Compound 19 (1 eq) in DMSO (1.25 vol) is added to a slurry of Na$^{14}$CN (1.4 eq) in DMSO (3 vol) maintaining the temperature between 30-40° C. The mixture is stirred for 1 hour then water (6 vol) is added followed by MTBE (4 vol). After stirring for 30 min, the layers are separated. The aqueous layer is extracted with MTBE (1.8 vol).

Synthesis of $^{14}$C-(2,2-difluoro-1,3-benzodioxol-5-yl)-cyclopropanecarbonitrile (Compound 24)

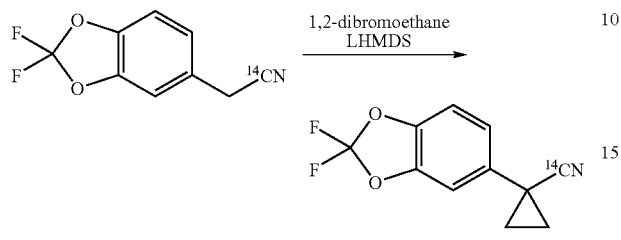

A mixture of compound 23 (1.0 eq) and 1,2-dibromoethane (1.8 eq) in THF (3 vol) is cooled to −10° C. via external chiller. 1 M LHMDS in THF (2.5 eq) is added via an addition funnel and at a rate to maintain the temperature in the reactor below 10° C. One hour after addition is complete, 20% w/v aq. citric acid (13 vol) is added via addition funnel maintaining the temperature in the reactor below 20 C. The external chiller is turned off and after stirring for 30 min the layers are separated. The organic layer is filtered and concentrated to afford crude compound 24 that is purified by chromatography.

Synthesis of $^{14}$C-1-(2,2-difluoro-1,3-benzodioxol-5-yl)-cyclopropanecarboxylic Acid (Compound 25)

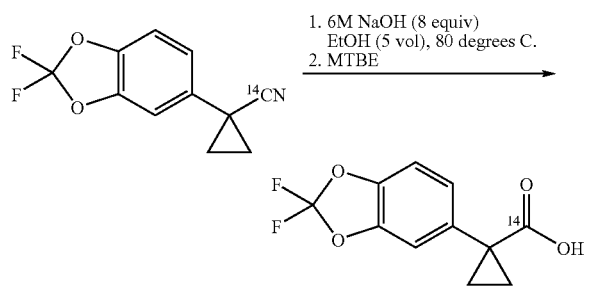

Compound 24 is hydrolyzed using 6 M NaOH (8 equiv) in ethanol (5 vol) at 80° C. overnight. The mixture is cooled to room temperature and ethanol is evaporated under vacuum. The residue is taken into water and MTBE. 1 M HCl is added to the mixture and the organic layer is filtered and concentrated to afford compound 25.

Synthesis of $^{14}$C-1-(2,2-difluoro-1,3-benzodioxol-5-yl)-cyclopropanecarbonyl Chloride (Compound 26)

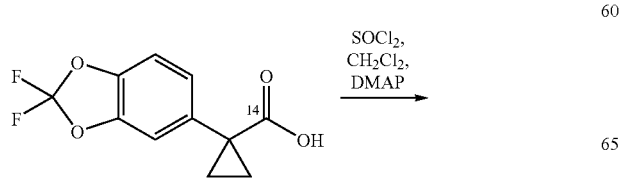

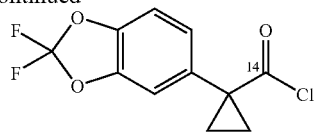

A mixture of Compound 25, 4-dimethylaminopyridine, and thionyl chloride (SOCl$_2$) in CH$_2$Cl$_2$ is stirred to produce compound 26, which may be further reacted with compound 6 without isolation.

Amine Moiety

Synthesis of tert-butyl-3-(3-methylpyridin-2-yl)benzoate (Compound 4)

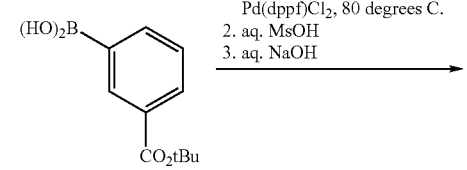

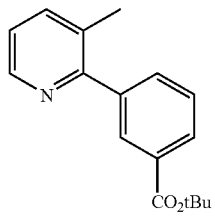

2-Bromo-3-methylpyridine (1.0 eq) is dissolved in toluene (12 vol). K$_2$CO$_3$ (4.8 eq) is added followed by water (3.5 vol) and the mixture heated to 65° C. under a stream of N$_2$ for 1 hour. 3-(t-Butoxycarbonyl)phenylboronic acid (1.05 eq) and Pd(dppf)Cl$_2$.CH$_2$Cl$_2$ (0.015 eq) are then added and the mixture is heated to 80° C. After 2 hours, the heat is turned off, water is added (3.5 vol) and the layers are allowed to separate. The organic phase is then washed with water (3.5 vol) and extracted with 10% aqueous methanesulfonic acid (2 eq MsOH, 7.7 vol). The aqueous phase is made basic with 50% aqueous NaOH (2 eq) and extracted with EtOAc (8 vol). The organic layer is concentrated to afford crude compound 4 (82%) that is used directly in the next step.

Synthesis of 2-(3-(tert-butoxycarbonyl)phenyl)-3-methylpyridine-1-oxide (Compound 5)

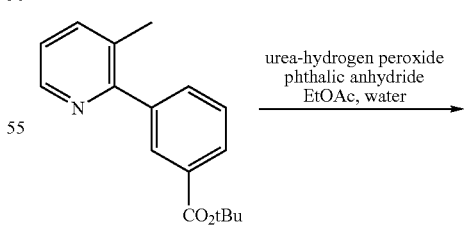

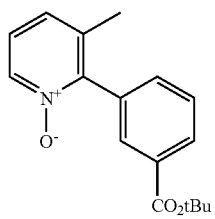

Compound 4 (1.0 eq) is dissolved in EtOAc (6 vol). Water (0.3 vol) is added followed by urea-hydrogen peroxide (3 eq). The phthalic anhydride (3 eq) is added portion-wise as a solid to maintain the temperature in the reactor below 45° C. After completion of phthalic anhydride addition, the mixture is heated to 45° C. After stirring for an additional 4 hours, the heat is turned off. 10% w/w aqueous $Na_2SO_3$ (1.5 eq) is added via addition funnel. After completion of $Na_2SO_3$ addition, the mixture is stirred for an additional 30 minutes and the layers separated. The organic layer is stirred and 10% w/w aq. $Na_2CO_3$ (2 eq) is added. After stirring for 30 minutes, the layers are allowed to separate. The organic phase is washed 13% w/v aq NaCl. The organic phase is then filtered and concentrated to afford crude compound 5 (95%) that is used directly in the next step.

Synthesis of tert-butyl-3-(6-amino-3-methylpyridin-2-yl)benzoate (Compound 6)

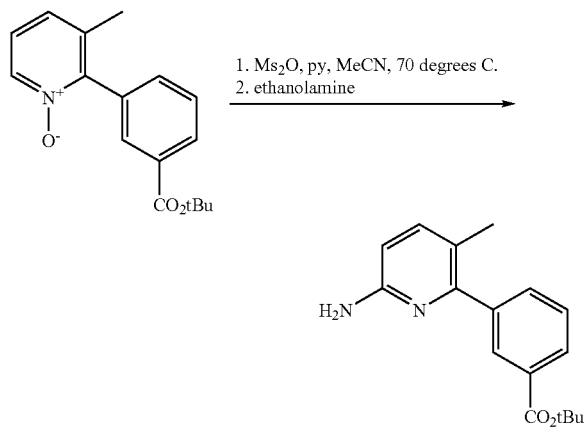

A solution of compound 5 (1 eq) and pyridine (4 eq) in MeCN (8 vol) is heated to 70° C. A solution of methanesulfonic anhydride (1.5 eq) in MeCN (2 vol) is added over 50 min via addition funnel maintaining the temperature at less than 75° C. The mixture is stirred for an additional 0.5 hours after complete addition. The mixture is then allowed to cool to ambient. Ethanolamine (10 eq) is added via addition funnel. After stirring for 2 hours, water (6 vol) is added and the mixture is cooled to 10° C. After stirring for NLT 3 hours, the solid is collected by filtration and washed with water (3 vol), 2:1 MeCN/water (3 vol), and MeCN (2×1.5 vol). The solid is dried to constant weight (<1% difference) in a vacuum oven at 50° C. with a slight $N_2$ bleed to afford compound 6 as a red-yellow solid (53% yield).

Synthesis of 3-(6-(1-(2,2-difluorobenzo[d][1,3]dioxol-5-yl)cyclopropanecarboxamido)-3-methylpyridin-2-yl)-t-butylbenzoate (Compound 8)

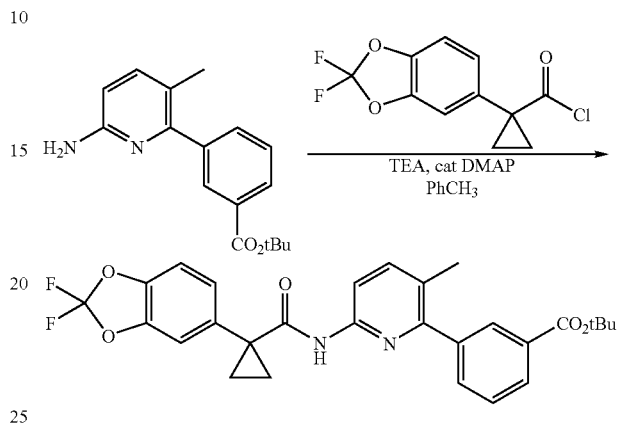

Compound 7 is dissolved in toluene (2.5 vol based on acid chloride) and added via addition funnel to a mixture of compound 6 (1 eq), dimethylaminopyridine (DMAP, 0.02 eq), and triethylamine (3.0 eq) in toluene (4 vol based on compound 6). After 2 hours, water (4 vol based on compound 6) is added to the reaction mixture. After stirring for 30 minutes, the layers are separated. The organic phase is then filtered and concentrated to afford a thick oil of compound 8 (quantitative crude yield). MeCN (3 vol based on crude product) is added and distilled until crystallization occurs. Water (2 vol based on crude product) is added and the mixture stirred for 2 h. The solid is collected by filtration, washed with 1:1 (by volume) MeCN/water (2×1 vol based on crude product), and partially dried on the filter under vacuum. The solid is dried to constant weight (<1% difference) in a vacuum oven at 60° C. with a slight $N_2$ bleed to afford 3-(6-(1-(2,2-difluorobenzo[d][1,3]dioxol-5-yl)cyclopropanecarboxamido)-3-methylpyridin-2-yl)-t-butylbenzoate as a brown solid.

Synthesis of Synthesis of 3-(6-(1-(2,2-difluorobenzo[d][1,3]dioxol-5-yl)cyclopropanecarboxamido)-3-methylpyridin-2-yl)benzoic Acid.HCL Salt (Compound 9)

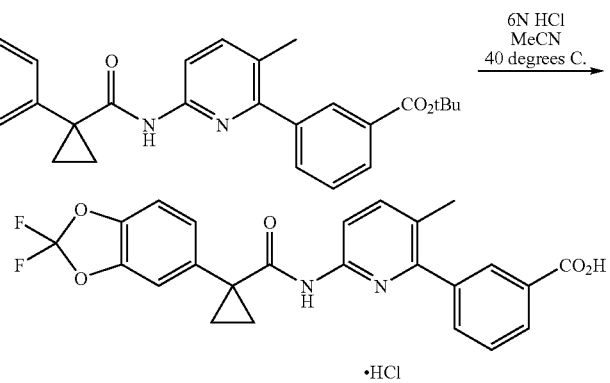

To a slurry of compound 8 (1.0 eq) in MeCN (3.0 vol) is added water (0.83 vol) followed by concentrated aqueous HCl (0.83 vol). The mixture is heated to 45±5° C. After stirring for 24 to 48 hours the reaction is complete and the mixture is allowed to cool to ambient. Water (1.33 vol) is added and the mixture stirred. The solid is collected by filtration, washed with water (2×0.3 vol), and partially dried on the filter under vacuum. The solid is dried to constant weight (<1% difference) in a vacuum oven at 60° C. with a slight $N_2$ bleed to afford compound 9 as an off-white solid.

Synthesis of 3-(6-(1-(2,2-difluorobenzo[d][1,3]dioxol-5-yl)cyclopropanecarboxamido)-3-methylpyridin-2-yl)benzoic Acid (Compound 1)

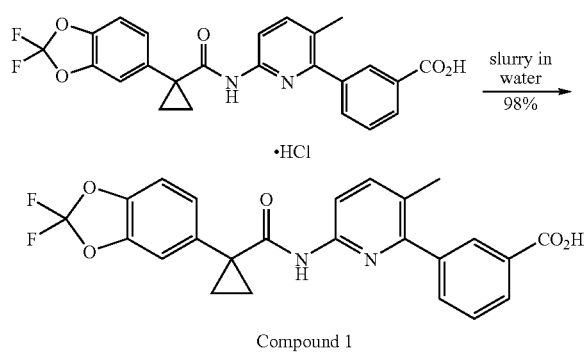

A slurry of 3-(6-(1-(2,2-difluorobenzo[d][1,3]dioxol-5-yl)cyclopropanecarboxamido)-3-methylpyridin-2-yl)benzoic acid.HCl (1 eq) in water (10 vol) is stirred at ambient temperature. A sample is taken after stirring for 24 hours. The sample is filtered and the solid washed with water (2×). The solid sample is submitted for DSC analysis. When DSC analysis indicates complete conversion to Compound 1, the solid is collected by filtration, washed with water (2×1.0 vol), and partially dried on the filter under vacuum. The solid is dried to constant weight (<1% difference) in a vacuum oven at 60° C. with a slight $N_2$ bleed to afford Compound 1 as an off-white solid (98% yield).

Synthesis of 3-(6-(1-(2,2-difluorobenzo[d][1,3]dioxol-5-yl)cyclopropanecarboxamido)-3-methylpyridin-2-yl)benzoic Acid (Compound 1) Using Water and Base

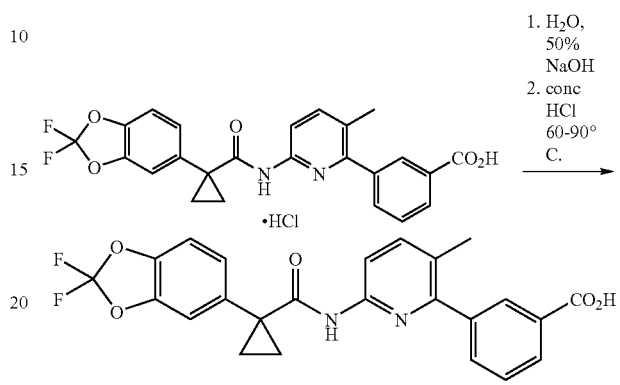

To a slurry of 3-(6-(1-(2,2-difluorobenzo[d][1,3]dioxol-5-yl)cyclopropanecarboxamido)-3-methylpyridin-2-yl)benzoic acid.HCl (1 eq) in water (10 vol) stirred at ambient temperature is added 50% w/w aq. NaOH (2.5 eq). The mixture is stirred for NLT 15 min or until a homogeneous solution. Concentrated HCl (4 eq) is added to crystallize Compound 1. The mixture is heated to 60° C. or 90° C. if needed to reduce the level of the t-butylbenzoate ester. The mixture is heated until HPLC analysis indicates NMT 0.8% (AUC) t-butylbenzoate ester. The mixture is then cooled to ambient and the solid is collected by filtration, washed with water (3×3.4 vol), and partially dried on the filter under vacuum. The solid is dried to constant weight (<1% difference) in a vacuum oven at 60° C. with a slight $N_2$ bleed to afford Compound 1 as an off-white solid (97% yield).

Synthesis of 3-(6-(1-(2,2-difluorobenzo[d][1,3]dioxol-5-yl)cyclopropanecarboxamido)-3-methylpyridin-2-yl)benzoic Acid (Compound 1) Directly from Benzoate

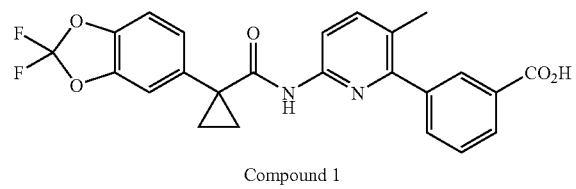

Compound 1

A solution of 3-(6-(1-(2,2-difluorobenzo[d][1,3]dioxol-5-yl)cyclopropanecarboxamido)-3-methylpyridin-2-yl)-t-butylbenzoate (1.0 eq) in formic acid (3.0 vol) is heated to 70±10° C. The reaction is continued until the reaction is complete (NMT 1.0% AUC 3-(6-(1-(2,2-difluorobenzo[d][1,3]dioxol-5-yl)cyclopropanecarboxamido)-3-methylpyridin-2-yl)-t-butylbenzoate) or heating for NMT 8 h. The mixture is allowed to cool to ambient. The solution is added to water (6 vol) heated at 50° C. and the mixture stirred. The mixture is then heated to 70±10° C. until the level of 3-(6-(1-(2,2-difluorobenzo[d][1,3]dioxol-yl)cyclopropanecarboxamido)-3-methylpyridin-2-yl)-t-butylbenzoate is NMT 0.8% (AUC). The solid is collected by filtration, washed with water (2×3 vol), and partially dried on the filter under vacuum. The solid is dried to constant weight (<1% difference) in a vacuum oven at 60° C. with a slight $N_2$ bleed to afford Compound 1 as an off-white solid.

An X-ray diffraction pattern calculated from a single crystal structure of Compound 1 in Form I is shown in FIG. 1. Table 1 lists the calculated peaks for FIG. 1.

TABLE 1

| Peak Rank | 2θ Angle [degrees] | Relative Intensity [%] |
| --- | --- | --- |
| 11 | 14.41 | 48.2 |
| 8 | 14.64 | 58.8 |
| 1 | 15.23 | 100.0 |
| 2 | 16.11 | 94.7 |
| 3 | 17.67 | 81.9 |
| 7 | 19.32 | 61.3 |
| 4 | 21.67 | 76.5 |
| 5 | 23.40 | 68.7 |
| 9 | 23.99 | 50.8 |
| 6 | 26.10 | 67.4 |
| 10 | 28.54 | 50.1 |

An actual X-ray powder diffraction pattern of Compound 1 in Form I is shown in FIG. 2. Table 2 lists the actual peaks for FIG. 2.

TABLE 2

| Peak Rank | 2θ Angle [degrees] | Relative Intensity [%] |
| --- | --- | --- |
| 7 | 7.83 | 37.7 |
| 3 | 14.51 | 74.9 |
| 4 | 14.78 | 73.5 |
| 1 | 15.39 | 100.0 |
| 2 | 16.26 | 75.6 |
| 6 | 16.62 | 42.6 |
| 5 | 17.81 | 70.9 |
| 9 | 21.59 | 36.6 |
| 10 | 23.32 | 34.8 |
| 11 | 24.93 | 26.4 |
| 8 | 25.99 | 36.9 |

Figure 3:
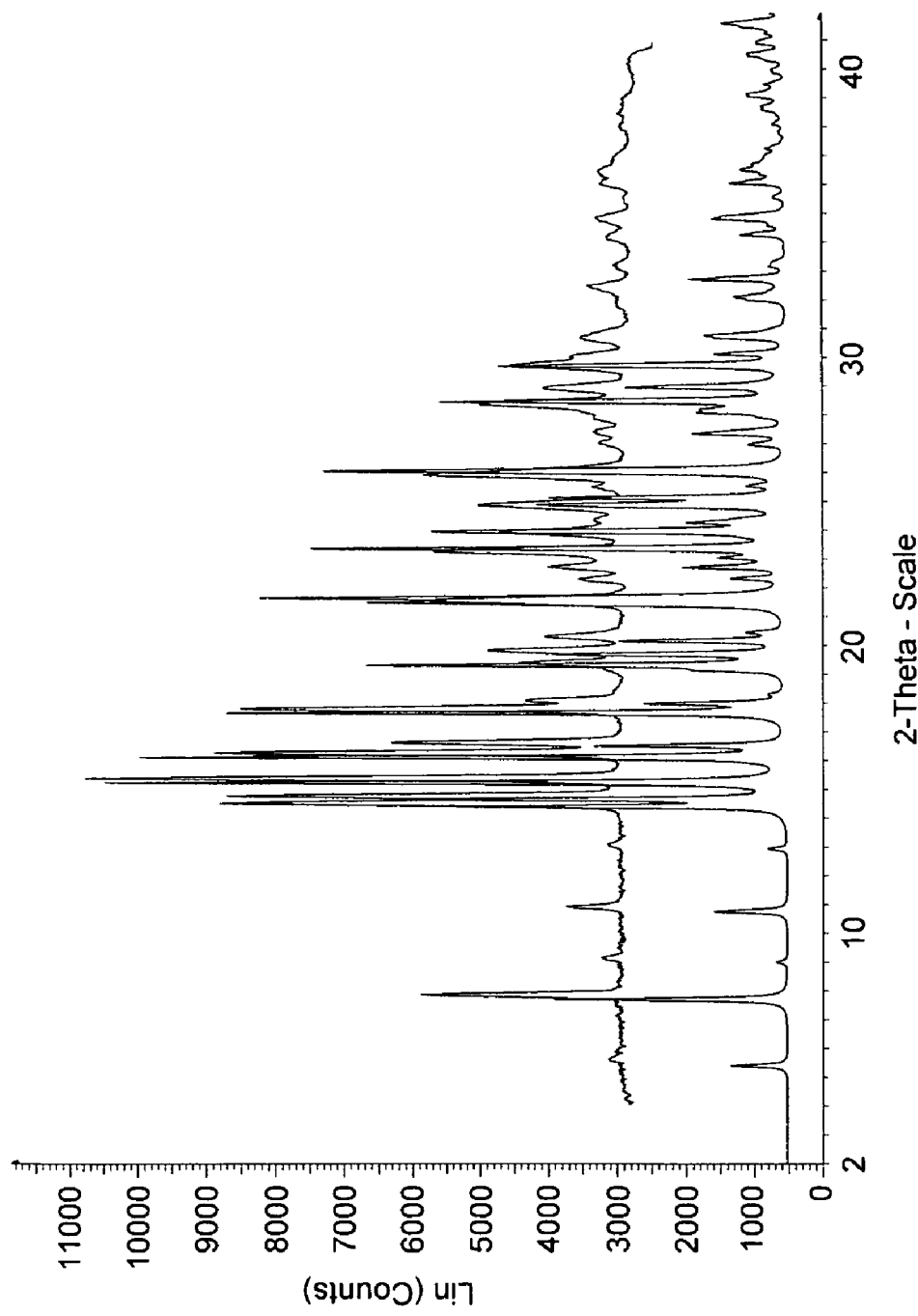
FIG. 3 is an overlay of an X-ray diffraction pattern calculated from a single crystal of Compound 1 in Form I, and an actual X-ray powder diffraction pattern of Compound 1 in Form I.

An overlay of an X-ray diffraction pattern calculated from a single crystal structure of Compound 1 in Form I, and an actual X-ray powder diffraction pattern of Compound 1 in Form I is shown in FIG. 3. The overlay shows good agreement between the calculated and actual peak positions, the difference being only about 0.15 degrees.

The DSC trace of Compound 1 in Form I is shown in FIG. 4. Melting for Compound 1 in Form I occurs at about 204° C.

Figure 6:
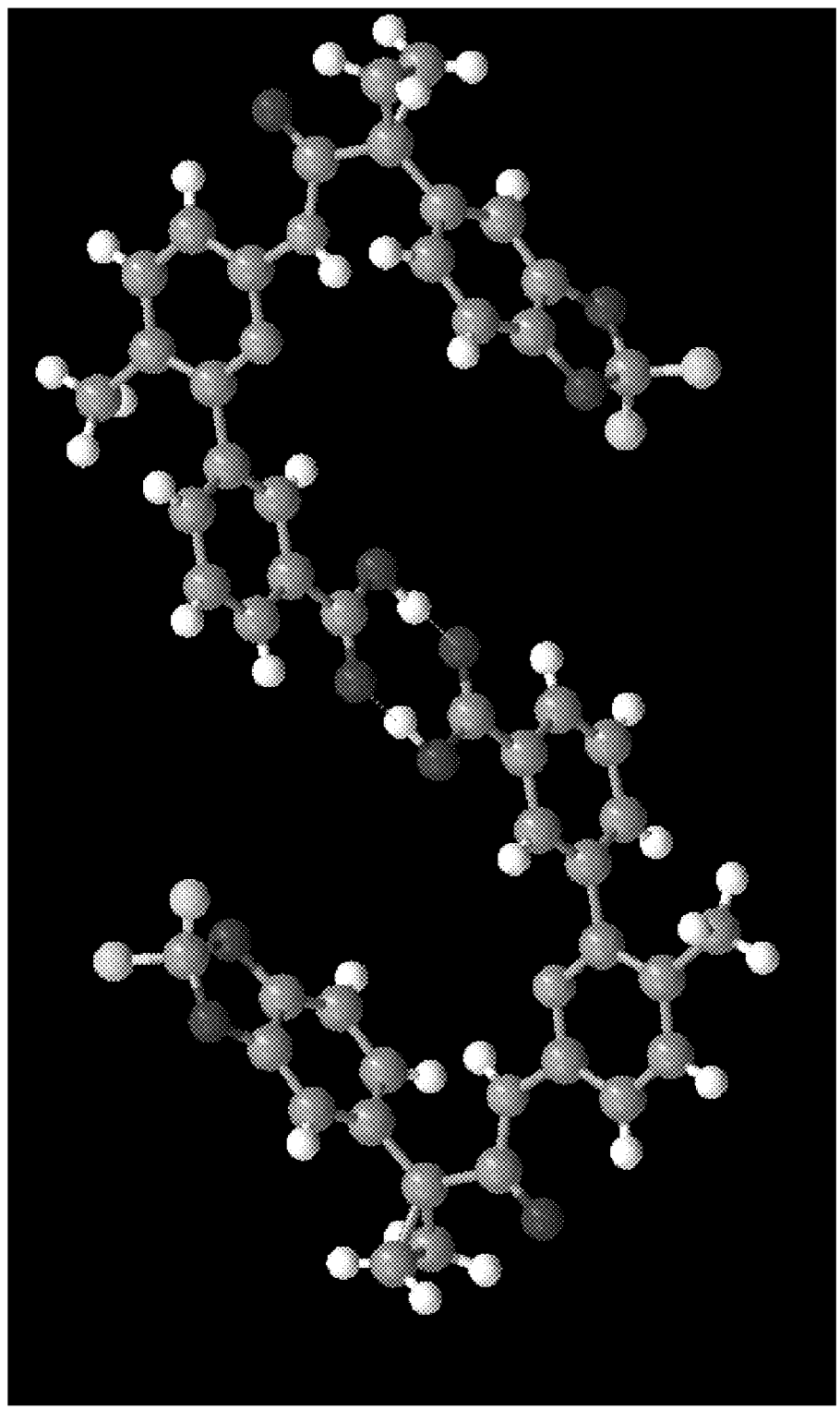
FIG. 6 is a conformational picture of Compound 1 in Form I based on single crystal X-ray analysis as a dimer formed through the carboxylic acid groups.
Figure 7:
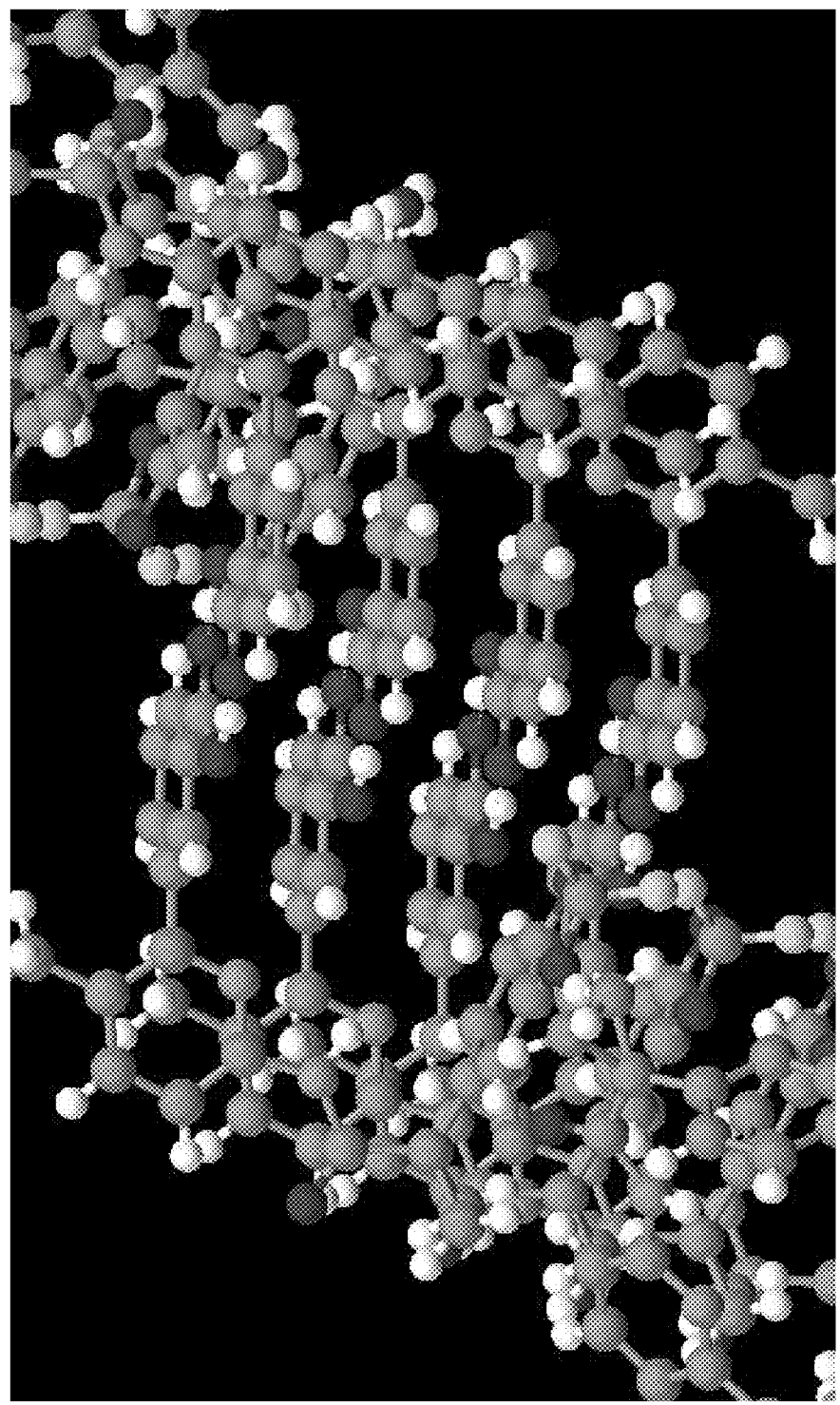
FIG. 7 is a conformational picture of Compound 1 in Form I based on single crystal X-ray analysis showing that the molecules are stacked upon each other.

Conformational pictures of Compound 1 in Form I based on single crystal X-ray analysis are shown in FIGS. 5-8. FIGS. 6-8 show hydrogen bonding between carboxylic acid groups of a dimer and the resulting stacking that occurs in the crystal. The crystal structure reveals a dense packing of the molecules. Compound 1 in Form I is monoclinic, $P2_1/n$, with the following unit cell dimensions: a=4.9626(7) Å, b=12.299 (2) Å, c=33.075 (4) Å, β=93.938(9)°, V=2014.0 Å$^3$, Z=4. Density of Compound 1 in Form I calculated from structural data is 1.492 g/cm$^3$ at 100 K.

Figure 11:
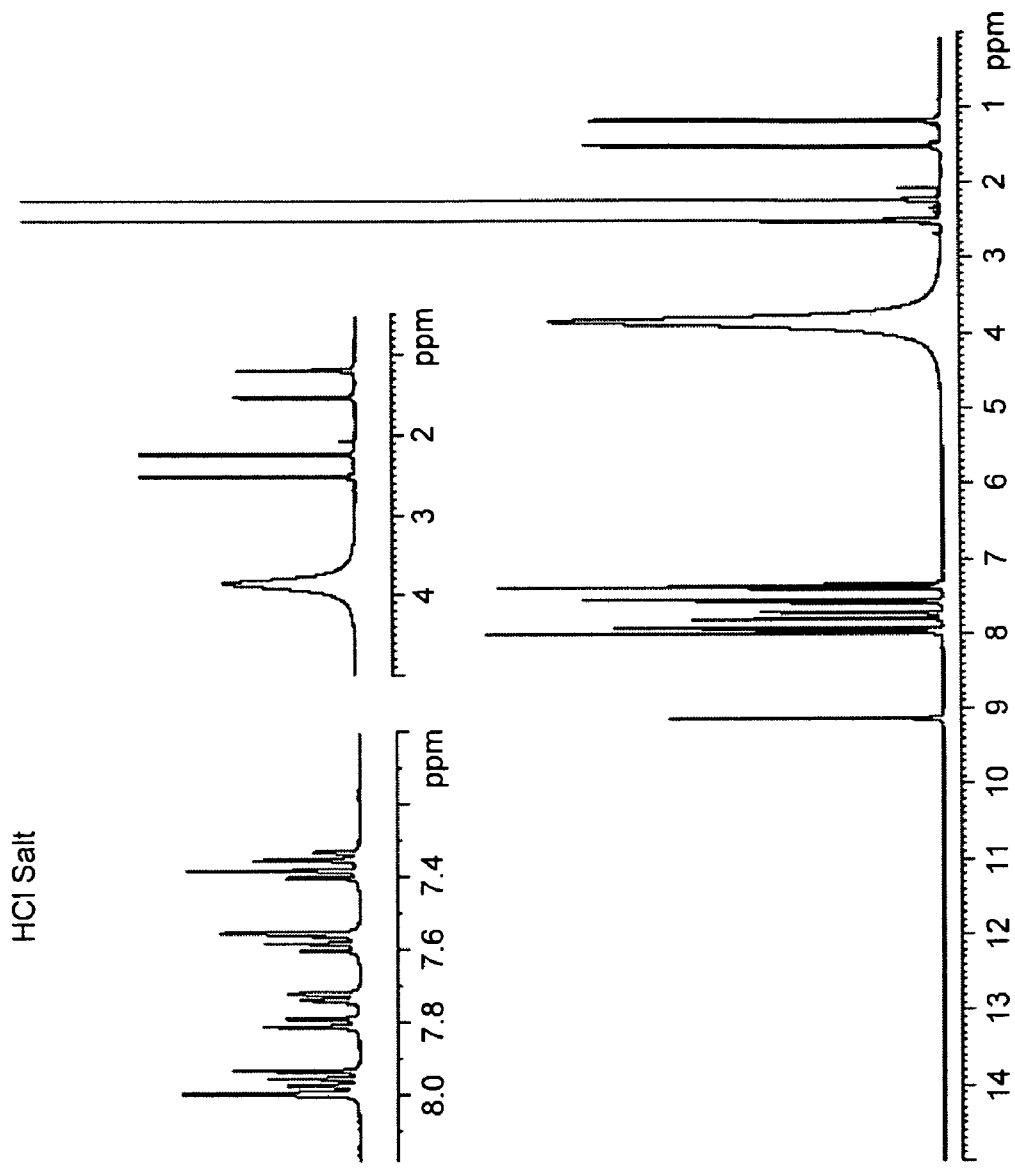
FIG. 11 is an $^1$HNMR analysis of Compound 1•HCl standard.

$^1$HNMR spectra of Compound 1 are shown in FIGS. 9-11 (FIGS. 9 and 10 depict Compound 1 in Form I in a 50 mg/mL, 0.5 methyl cellulose-polysorbate 80 suspension, and FIG. 11 depicts Compound 1 as an HCl salt).

Table 3 below recites additional analytical data for Compound 1.

TABLE 3

| Cmpd. No. | LC/MS M + 1 | LC/RT min | NMR |
| --- | --- | --- | --- |
| 1 | 453.3 | 1.93 | H NMR (400 MHz, DMSO-d6) 9.14 (s, 1H), 7.99-7.93 (m, 3H), 7.80-7.78 (m, 1H), 7.74-7.72 (m, 1H), 7.60-7.55 (m, 2H), 7.41-7.33 (m, 2H), 2.24 (s, 3H), 1.53-1.51 (m, 2H), 1.19-1.17 (m, 2H) |

The invention claimed is:

1. A process for preparing Compound 1:

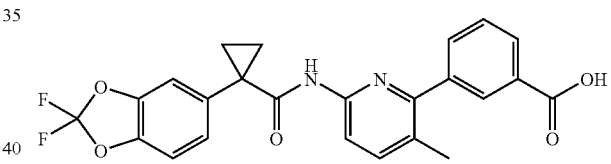

comprising the steps of:
i) providing 2-bromo-3-methylpyridine (compound 2) and 3-(t-butoxycarbonyl)phenylboronic acid (compound 3),

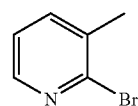

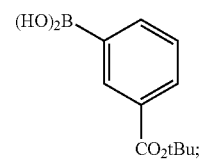

ii) cross coupling compound 2 and compound 3 in a biphasic mixture comprising water, a first organic solvent, a first base, and a transition metal catalyst to produce compound 4,

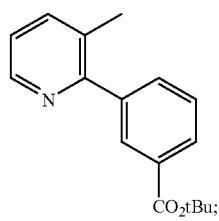
4 iii) oxidizing compound 4 to produce compound 5,

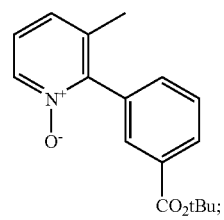
5 iv) adding an amine group to the 6 position of the pyridyl moiety to produce compound 6,

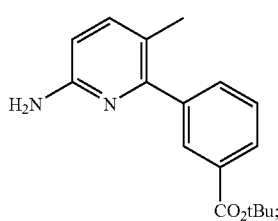
6 v) reacting compound 6 with compound 7,

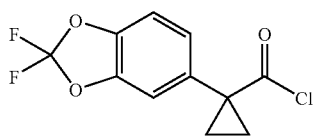
7 in a second organic solvent in the presence of a second base to produce compound 8,

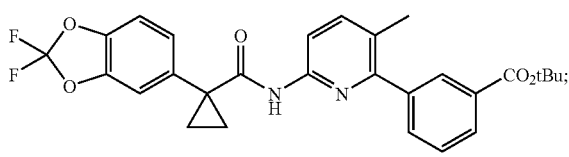
8 vi) de-esterifying compound 8 in a biphasic mixture comprising water, a third organic solvent, and a first acid to produce compound 9,

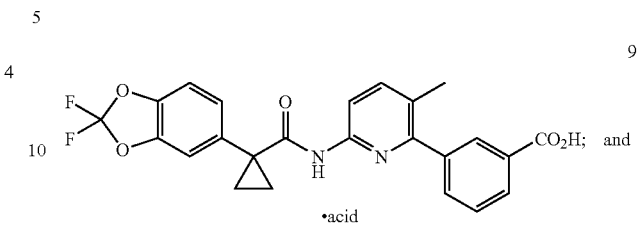
9

·acid vii) slurrying or dissolving compound 9 in a solvent for an effective amount of time to produce Compound 1.

2. The process of claim 1, wherein the first organic solvent is an aprotic solvent.

3. The process of claim 1, wherein the first organic solvent is toluene.

4. The process of claim 1, wherein the first organic solvent is a protic solvent.

5. The process of claim 1, wherein the first organic solvent is selected from methanol, ethanol, or isopropanol.

6. The process of claim 1, wherein the first base is an inorganic base.

7. The process of claim 1, wherein the first base is potassium carbonate.

8. The process of claim 1, wherein the transition-metal catalyst is a palladium-based catalyst.

9. The process of claim 1, wherein the palladium-based catalyst is Pd(dppf)Cl$_2$.

10. The process of claim 1, wherein the cross coupling reaction is run at between 60° C. and 100° C.

11. The process of claim 1, wherein the oxidation reaction is carried out using a peroxide.

12. The process of claim 1, wherein the oxidation reaction is carried out using peracetic acid.

13. The process of claim 1, wherein the oxidation reaction is carried out in the presence of an anhydride.

14. The process of claim 1, wherein the oxidation reaction is carried out in the presence of phthalic anhydride.

15. The process of claim 1, wherein the oxidation reaction is run at between 25° C. and 65° C.

16. The process of claim 1, wherein the amination reaction is carried out in the presence of a sulfonyl compound.

17. The process of claim 1, wherein the amination reaction is carried out in the presence of methanesulfonic anhydride.

18. The process of claim 1, wherein the amination reagent used in the amination reaction is an alcohol amine.

19. The process of claim 1, wherein the amination reagent used in the amination reaction is ethanolamine.

20. The process of claim 1, wherein the second organic solvent is an aprotic solvent.

21. The process of claim 1, wherein the second organic solvent is toluene.

22. The process of claim 1, wherein the second base is an organic base.

23. The process of claim 1, wherein the second base is triethylamine.

24. The process of claim 1, wherein the reaction between compound 6 and compound 7 is carried out in the presence of a catalytic amine.

25. The process of claim 1, wherein the reaction between compound 6 and compound 7 is carried out in the presence of a catalytic amount of dimethylaminopyridine.

26. The process of claim 1, wherein the third organic solvent is an aprotic solvent.

27. The process of claim 1, wherein the third organic solvent is acetonitrile.

28. The process of claim 1, wherein the first acid is an inorganic acid.

29. The process of claim 1, wherein the first acid is hydrochloric acid.

30. The process of claim 1, wherein the de-esterification reaction is run at between 20° C. and 60° C.

31. The process of claim 1, wherein the solvent of step vii) is selected from water or a 50% methanol/water mixture.

32. The process of claim 1, wherein the solvent of step vii) is water.

33. The process of claim 1, wherein the effective amount of time is between 2 and 24 hours.

34. The process of claim 1, further comprising the step of filtering the slurry of Compound 1 or concentrating the solution of Compound 1 to effect recrystallization and filtering the recrystallized Compound 1.

35. A process for preparing Compound 1 comprises the step of:
i) reacting compound 6,

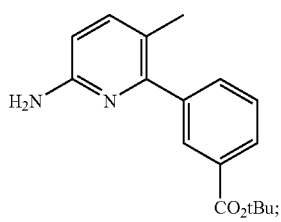

6 with compound 7,

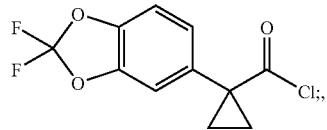

7 in a second organic solvent in the presence of a second base to produce compound 8,

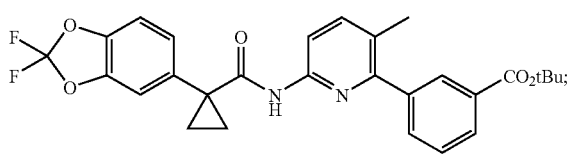

8 ii) de-esterifying compound 8 in a biphasic mixture comprising water, a third organic solvent, and a first acid to produce compound 9,

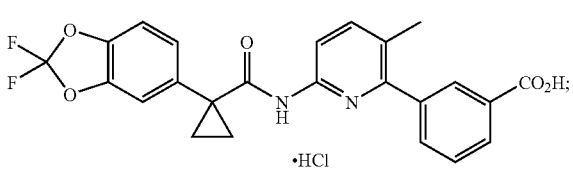

9 iii) slurrying or dissolving compound 9 in a solvent for an effective amount of time to produce Compound 1.

* * * * *